United States Patent [19]
Katz et al.

[11] Patent Number: 5,840,494
[45] Date of Patent: Nov. 24, 1998

[54] METHOD FOR MOLECULAR STAGING OF PROSTATE CANCER

[75] Inventors: Aaron E. Katz, Armonk; Ralph Buttyan; Anthony Raffo, both of New York; Carl A. Olsson, Larchmont, all of N.Y.

[73] Assignee: The Trustees of Columbia University in the City of New York, New York, N.Y.

[21] Appl. No.: 844,024

[22] Filed: Apr. 18, 1997

Related U.S. Application Data

[63] Continuation of Ser. No. 229,391, Apr. 15, 1994, abandoned.
[51] Int. Cl.[6] .............................. C12Q 1/68; C07H 21/04; C12P 19/34
[52] U.S. Cl. ............................... 435/6; 435/91.2; 435/63; 435/64; 536/24.31; 536/24.33; 935/8; 935/16; 935/17; 935/78
[58] Field of Search .............................. 435/6, 91.2, 91.5, 435/91.51; 536/24.31, 24.33; 436/63, 64, 164, 172; 935/8, 16, 17, 18, 78

[56] References Cited

FOREIGN PATENT DOCUMENTS

0520794A1 12/1992 European Pat. Off. .

OTHER PUBLICATIONS

Anscher, M.S. and Prosnitz, L.R. (1987) "Postoperative radiotherapy for patient with carcinoma of the prostate undergoing radical prostatectomy with positive surgical margins, seminal vesicle involvement and/or penetration throught the capsule." *J. Urol.* 138: 1407–1412 (Exhibit 3).

Batson, O.V. (1940) "The function of the vertebral veins and their role in the spread of metastasis." *Ann. Surg.* 112: 138–142 (Exhibit 4).

Benson, M.C., et al. (1992) "Prostate Specific Antigen Density: A means of distinguishing benign prostatic hypertrophy and prostate cancer." *J. Urol.* 147: 815–816 (Exhibit 5).

Catalona, W.J., et al. (1985) Nerve–sparing radical prostatectomy: Extraprostatic tumor extension and preservation of erectile function. *J. Urol.* 134: 1149–1151 (Exhibit 6 ).

Digby, M., et al. (1989) "Human prostate specific antigen (PSA) gene: structure and linkage to the kallikrein–like gene, hGK–1." *Nucl. Acids Res.* 17:2137 (Exhibit 8).

Dodds, P.R., et al. (1981) "The role of the vertebral veins in the dissemination of prostate cancer." *J. Urol.* 126: 753–755 (Exhibit 9).

Epstein, J., et al. (1993) "Correlation of pathologic findings after radical retropubic prostatectomy." *Cancer* 71: 3582–3593 (Exhibit 10).

Gerber, G.S. et al. (1992) "Local staging of prostate cancer by tumor volume, prostate–specific antigen, and transrectal ultrasound." *Urology* 40: 311–316 (Exhibit 11).

Hamdy, F.C., et al. (1979) "Circulating prostate specific antigen–positive cells correlate with metastatic prostate cancer." *Brit. J. Urol.* 69: 392–396 (Exhibit 12).

Horoszewicz, J.S., et al. (1983) "LNCaP model of human prostatic carcinoma." *Can. Res.* 43: 1809–1817 (Exhibit 13).

Hricak, H., et al. (1987) "Prostatic carcinoma: Staging by clinical assessment, CT, and MR imaging." *Radiology* 162: 331–336 (Exhibit 14).

Hudson, M.A., et al. (1989) "Clinical use of prostate specific antigen density in patients with prostate cancer." *J. Urol.* 142: 1011–1017 (Exhibit 15).

Klobeck, H.G., et al. (1989) "Genomic sequences of human prostate specific antigen (PSA)." *Nucleic Acids Res.* 17: 3981 (Exhibit 16).

Lanzillo, J.J. (1990) "Preparation of digoxigenin–labeled probes by the polymerase chain reaction." *Biotech.* 8: 620–622 (Exhibit 17).

Mukamel, E., et al. (1982) "Pitfalls in preoperative staging in prostate cancer." *Urol.* 30: 318–321 (Exhibit 19).

Oesterling, J., et al. (1993) "The use of prostate–specific antigen in staging patients with newly diagnosed prostate cancer." *J.A.M.A.* 269: 57–60 (Exhibit 20).

Platt, J.F., et al. (1987) "The accuracy of CT in the staging of the prostage." *Amer. J. Roent.* 149: 315–318 (Exhibit 21).

Seaman, E., et al. (1993) "The use of PSAD to predict D–O prostatic carcinoma." *J. Urol.* 149: 300A (Exhibit 22).

Wang, M.C., et al. (1979) "Purification of a human prostate specific antigen." *Invest. Urol.* 17: 159–163 (Exhibit 23).

Winter, H.I., et al. (1991) "Preoperative prostate–specific antigen in predicting pathological stage and grade after radical prostatectomy." *Urology* 38: 202–205 (Exhibit 24).

Kawasaki et al. PCR Protocols: A Guide to Methods & Applications (1989), pp. 21–27, Academic Press, Inc, NY, Innis et al (Editors).

Fiss et al, Journal Clinical Microbiology (1992) 30: 1220–1224.

Holmstrom et al, Analytical Biochemistry (1993) 209: 278–283.

Hermanek et al, in Oxford Textbook of Oncology, vol. 1, 1995, Oxford Univ Press, NY, pp. 880–887.

Boehringer Mannheim Catalog, 1994, p. 61.

Moreno et al Cancer research (1992) 52: 6110–6112.

Deguchi et al Cancer Research (1993) 53: 5350–5354.

Chiarodo, Cancer Research (1991) 51: 2498–2505.

Katz et al, Urological Research (1993) 21: 462, Abstract 082.

*Primary Examiner*—Carla J. Myers
*Attorney, Agent, or Firm*—John P. White; Cooper & Dunham LLP

[57] ABSTRACT

This invention provides a method of determining the stage of prostate cancer in a human subject using a sample of peripheral blood from a human subject. The invention uses reverse transcriptase-PCR to detect the mRNA encoding prostate specific antigen (PSA) in circulating cells expressing PSA. The invention further uses digoxigenin enhancement of the resultant cDNA signal. The method has an overall sensitivity capable of detecting one PSA expressing cell per 100,000 cells. The method produced no false positives and had a superior detection selectivity for patients with nonlocalized prostate cancer.

5 Claims, 10 Drawing Sheets

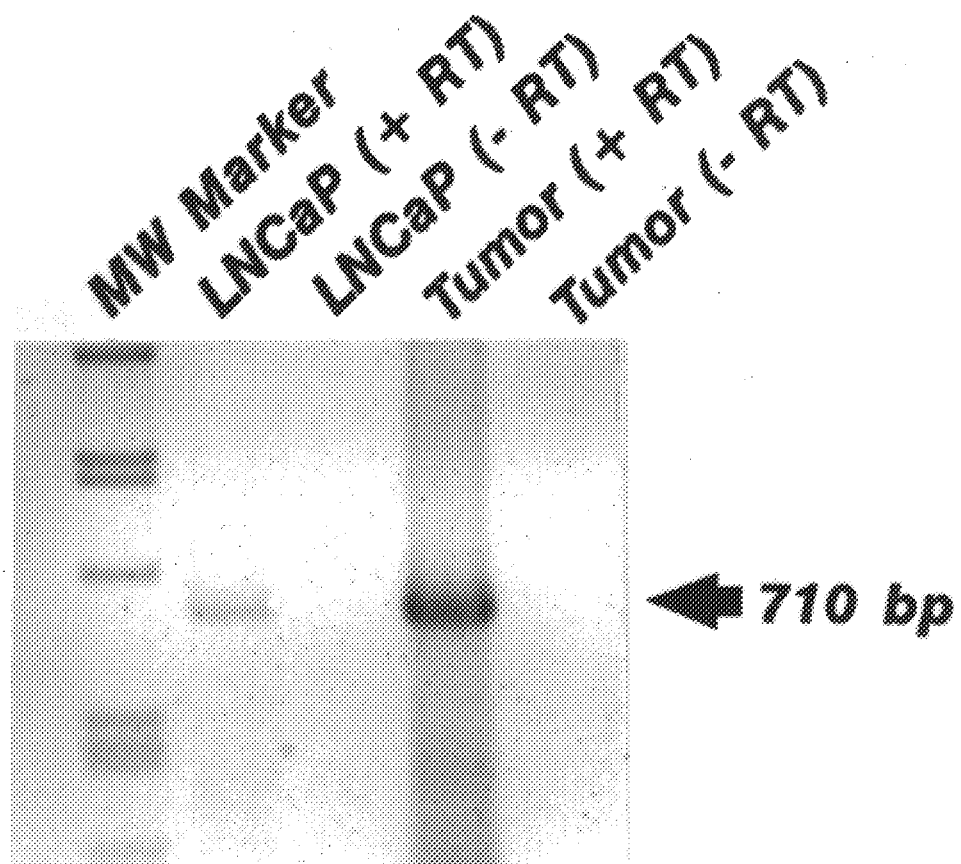

PSA

G3-PDH

Ethidium Bromide Detection

Enhanced Detection

FIG. 6A

```
AAGTTCCCT  TCTCCCAGTC  CAAGACCCCA  AATCACCACA  AAGGACCCAA  TCCCCAGACT   60
CAAGATATGG  TCTGGGCGCT  GTCTTGTGTC  TCCTACCCTG  ATCCCTGGGT  TCAACTCTGC  120
TCCCAGAGCA  TGAAGCCTCT  CCACCAGCAC  CAGCCACCAA  CCTGCAAACC  TAGGGAAGAT  180
TGACAGAATT  CCCAGCCTTT  CCCAGCTCCC  CCTGCCCATG  TCCCAGGACT  CCCAGCCTTG  240
```

FIG. 6B

```
GTTCTCTGCC CCCGTGTCTT TTCAAACCCA CATCCTAAAT CCATCTCCTA TCCGAGTCCC      300

CCAGTTCCTC CTGTCAACCC TGATTCCCCT GATCTAGCAC CCCCTCTGCA GGTGCTGCAC      360

CCCTCATCCT GTCTCGG ATT GTG GGA GGC TGG GAG TGC GAG AAG CAT TCC         410
                   Ile Val Gly Gly Trp Glu Cys Glu Lys His Ser
                    1               5                      10

CAA CCC TGG CAG GTG CTT GTA GCC TCT CGT GGC AGG GCA GTC TGC GGC         458
Gln Pro Trp Gln Val Leu Val Ala Ser Arg Gly Arg Ala Val Cys Gly
             15                  20                  25

GGT GTT CTG GTG CAC CCC CAG TGG GTC CTC ACA GCT ACC CAC TGC ATC         506
Gly Val Leu Val His Pro Gln Trp Val Leu Thr Ala Thr His Cys Ile
         30                  35                  40

AGG AAC AAA AGC GTG ATC TTG CTG GGT CGG CAC AGC CTG TTT CAT CCT         554
Arg Asn Lys Ser Val Ile Leu Leu Gly Arg His Ser Leu Phe His Pro
     45                  50                  55

GAA GAC ACA GGC CAG GTA TTT CAG GTC AGC CAC TTC CCA CAC CCG             602
Glu Asp Thr Gly Gln Val Phe Gln Val Ser His Phe Pro His Pro
 60                  65                  70                  75
```

FIG. 6C

```
CTC TAC GAT ATG AGC CTC CTG AAG AAT CGA TTC CTC AGG CCA GGT GAT    650
Leu Tyr Asp Met Ser Leu Leu Lys Asn Arg Phe Leu Arg Pro Gly Asp
             80                      85                      90

GAC TCC AGC CAC GAC CTC ATG CTG CTC CGC CTG TCA GAG CCT GCC GAG    698
Asp Ser Ser His Asp Leu Met Leu Leu Arg Leu Ser Glu Pro Ala Glu
         95                     100                     105

CTC ACG GAT GCT ATG AAG GTC ATG GAC CTG CCC ACC CAG GAG CCA GCA    746
Leu Thr Asp Ala Met Lys Val Met Asp Leu Pro Thr Gln Glu Pro Ala
        110                     115                     120

CTG GGG ACC ACC TGC TAC GCC TCA GGC TGG GGC AGC ATT GAA CCA GAG    794
Leu Gly Thr Thr Cys Tyr Ala Ser Gly Trp Gly Ser Ile Glu Pro Glu
    125                     130                     135

GAG TTC TTG ACC CCA AAG AAA CTT CAG TGT GTG GAC CTC CAT GTT ATT    842
Glu Phe Leu Thr Pro Lys Lys Leu Gln Cys Val Asp Leu His Val Ile
140                     145                     150                 155
```

FIG. 6D

```
TCC AAT GAC GTG TGT GCG CAA GTT CAC CCT CAG AAG GTG ACC AAG TTC    890
Ser Asn Asp Val Cys Ala Gln Val His Pro Gln Lys Val Thr Lys Phe
            160                 165                 170

ATG CTG TGT GCT GGA CGC TGG ACA GGG GGC AAA AGC ACC TGC TCG GGT    938
Met Leu Cys Ala Gly Arg Trp Thr Gly Gly Lys Ser Thr Cys Ser Gly
        175                 180                 185

GAT TCT GGG GGC CCA CTT GTC TGT AAT GGT GTG CTT CAA GGT ATC ACG    986
Asp Ser Gly Gly Pro Leu Val Cys Asn Gly Val Leu Gln Gly Ile Thr
        190                 195                 200

TCA TGG GGC AGT GAA CCA TGT GCC CTG CCC GAA AGG CCT TCC CTG TAC   1034
Ser Trp Gly Ser Glu Pro Cys Ala Leu Pro Glu Arg Pro Ser Leu Tyr
        205                 210                 215

ACC AAG GTG GTG CAT TAC CGG AAG TGG ATC AAG GAC ACC ATC GTG GCC   1082
Thr Lys Val Val His Tyr Arg Lys Trp Ile Lys Asp Thr Ile Val Ala
        220                 225                 230         235

AAC CCC TGAGCACCCC TATCAACTCC CTATTGTAGT AAACTTGGAA CCTTGGAAAT    1138
Asn Pro

GACCAGGCCA AGACTCAGGC CTCCCCAGTT CTACTGACCT TTGTCCTTAG GTGTGAGGTC  1198
```

FIG. 6E

```
CAGGGTTGCT AGGAAAAGAA ATCAGCAGAC ACAGGTGTAG ACCAGAGTGT TTCTTAAATG   1258

GTGTAATTTT GTCCTCTCTG TGTCCTGGGG AATACTGGCC ATGCCTGGAG ACATATCACT   1318

CAATTCTCT  GAGGACACAG ATAGGATGGG GTGTCTGTGT TATTTGTGGG GTACAGAGAT   1378

GAAAGAGGGG TGGGATCCAC ACTGAGAGAG TGGAGAGTGA CATGTGCTGG ACACTGTCCA   1438

TGAAGCACTG AGCAGAAGCT GGAGGCACAA CGCACCAGAC ACTCACAGCA AGGATGGAGC   1498

TGAAAACATA ACCCACTCTG TCCTGGAGGC ACTGGGAAGC CTAGAGAAGG CTGTGAACCA   1558

AGGAGGGAGG GTCTTCCTTT GGCATGGGAT GGGGATGAAG TAAGGAGAGG GACTGACCCC   1618

CTGGAAGCTG ATTCACTATG GGGGAGGTG  TATTGAAGTC CTCCAGACAA CCCTCAGATT   1678

TGATGATTTC CTAGTAGAAC TCACAGAAAT AAAGAGCTGT TATACTGTGA A            1729
```

METHOD FOR MOLECULAR STAGING OF PROSTATE CANCER

This is a continuation of application Ser. No. 08/229,391, filed Apr. 15, 1994, which is now abandoned.

This invention was made with support under Grant No. CA58089 from the National Cancer Institute. Accordingly, the U.S. government has certain rights in the invention.

BACKGROUND OF THE INVENTION

Throughout this application, various publications are referenced. Full citations for these references may be found at the end of the specification immediately preceding the claims. The disclosure of these publications is hereby incorporated by reference into this application to describe more fully the art to which this invention pertains. Approximately 60% of newly diagnosed patients with prostate cancer will have established metastasis at the time of diagnosis (2). Once the disease has spread to distant rites, the overall prognosis is poor (3,4). Organ-confined prostate cancer should be curative upon removal of the gland, however screening modalities to assess early metastases often fail to identify a significant subset of patients with locally invasive disease (involving penetration of the capsule or seminal vesicle). Recent studies report that up to 40–50% of patients who were thought to have clinically localized disease were found to be understaged subsequent to radical surgery (5,6, 7). This failure rate creates a clinical dilemma since operative therapy is not the appropriate treatment modality for these patients. Clearly, development of a more sensitive means to identify patients with micrometastic, locally invasive disease is warranted.

Prostate cancer metastases are more frequently found in the pelvic lymph nodes and on bone and these are sites surveyed most aggressively in patients diagnosed with prostate cancer. The involvement of draining lymph nodes in the dissemination of this cancer is expected, given our understanding of solid tumor behavior. The means by which the prostate cancer cells target the bone is debated, but suspected to involve blood vessels to the lower spine, specifically the vertebral venous plexus (8,9). This spread presupposes that prostate cancer cells are shed into the blood stream and implies a role for hematogenous dissemination in prostate cancer progression.

Indeed, a preliminary study showing that prostate cells can be putatively identified in blood specimens of patients with metastatic prostate cancer supports the concept of blood-borne metastasis (10).

This previous study reported that cells synthesizing prostate specific antigen (PSA) were present in the circulating blood of patients with prostate specific antigen (PSA) were present in the circulating blood of patients with prostate cancer metastases. Since the expression of this protein is restricted to epithelial cells of the prostate gland, the detection of PSA synthesizing cells in the circulation indicates an unexpected and potentially abnormal situation. Here, we describe our development of an extremely sensitive "enhanced" PCR-based assay that allows us to identify PSA-synthesizing cells even when they are highly diluted in a population of peripheral lymphocytes. When this assay was applied to RNA extracted from peripheral blood cells of prostate cancer patients, it enabled us to distinguish the overwhelming majority of patients with overt metastatic disease as well as patients with locally invasive tumors that were understaged by conventional screening modalities (i.e. digital rectal exam, CT-scan and/or endorectal MRI). The remarkable accuracy of this assay in upstaging patients with apparent clinically localized disease could eliminate a significant number of prostate cancer patients from unnecessary operations and potentially increase the cure rate in patients who are treated by radical prostatectomy. Since this simple assay involves the molecular detection of a prostate-specific gene product, it represents the first reported instance of molecular staging of a solid human tumor.

SUMMARY OF THE INVENTION

This invention provides a method of determining the stage of prostate cancer in a human subject using a sample of peripheral blood from a human subject. The invention uses reverse transcriptase-PCR to detect the mRNA encoding prostate specific antigen (PSA) in circulating cells expressing PSA. The invention further uses digoxigenin enhancement of the resultant cDNA signal. The method has an overall sensitivity capable of detecting one PSA expressing cell per 100,000 cells. The method produced no false positives and had a superior detection selectivity for patients with nonlocalized prostate cancer.

BRIEF DESCRIPTION OF THE FIGURES

FIG. 1 RT-PCR assay identifies expression of PSA in the LNCaP cell line in a specimen of human prostate cancer. Total RNA was extracted from LNCaP cells and from a human prostate tumor. Aliquots were assayed for the presence of the diagnostic 710 bp PSA-specific PCR DNA fragment following treatment with oligo-dT with (+RT) or without (−RT) reverse transcriptase. The 710 bp PSA fragment was detected by UV transillumination of the ethidium bromide stained agarose gel following electrophoresis.

FIG. 5A; total RNA was extracted from peripheral blood lymphocytes of patients with localized and metastatic prostate cancer. This RNA was assayed by RT-PCR for PSA. Three specimens, as well as the LNCaP and prostate tumor control RNA demonstrate the presence of this fragment following ethidium bromide staining of the agarose gel. FIG. 5B; demonstrate enhanced detection of the 710 bp PSA fragment. Luminescent substrate and autoradiography allowed the detection of 7 additional positive specimens in this group of patients.

FIGS. 6A–6E Nucleic acid sequence of the cDNA encoding the PSA protein.

DETAILED DESCRIPTION OF THE INVENTION

Figure 2A:
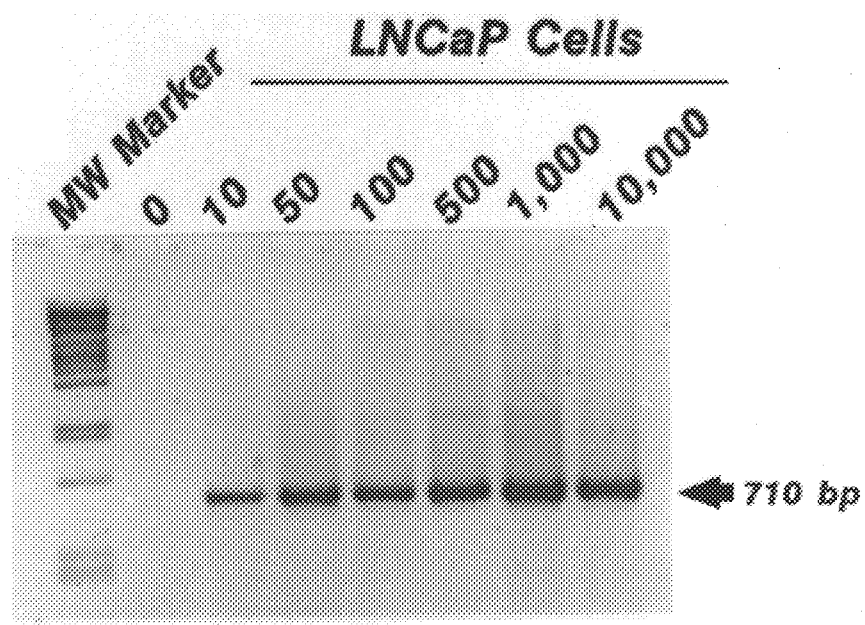
FIGS. 2A and 2B Sensitivity of RT-PCR assay determined by analysis of diluted LNCaP cells. RNA was extracted from serial dilutions of LNCaP cells in $10^6$ cultured B lymphocytes and was assayed by RT-PCR for PSA. The 710 bp PSA-PCR fragment could be amplified only from specimens containing LNCaP cells (FIG. 2A). Human G3PDH primers were utilized in a parallel reaction and these primers amplified the appropriate 983 bp fragment from all specimens (FIG. 2B).

This invention provides a method of determining the stage of prostate cancer in a human subject which comprises: collecting a sample of peripheral blood from a human subject; extracting mRNA molecules from the peripheral blood; amplifying a cDNA molecule encoding the PSA protein which comprises: (i) contacting the mRNA molecule extract with a nucleic acid molecule primer capable of specifically hybridizing to a nucleic acid sequence site included within the mRNA encoding the PSA protein under conditions allowing the primer to specifically hybridize to the mRNA encoding the PSA protein; (ii) contacting the composition of (i) with reverse transcriptase under conditions allowing the reverse transcriptase to transcribe a single stranded cDNA molecule copy of the mRNA molecule encoding the PSA protein; (iii) heat denaturing the cDNA and mRNA molecule of composition (ii); (iv) contacting the composition of (iii) with a first primer capable of specifically hybridizing to a first unique nucleic acid molecule sequence site located on the cDNA molecule complementary to the mRNA encoding the PSA protein under conditions allowing the first primer to specifically hybridize with the first unique nucleic acid molecule sequence site; (v) contacting the composition of (iv) with DNA polymerase under conditions allowing the DNA polymerase to synthesize a double stranded cDNA molecule encoding the PSA protein using the first primer to initiate synthesis and the single-stranded cDNA molecule as a template; (vi) heat denaturing the double-stranded cDNA molecule of composition (v); (vii) contacting the composition of (vi) with the first primer and a second nucleic acid molecule primer capable of specifically hybridizing with a second unique nucleic acid molecule sequence site wherein the second unique nucleic acid sequence site is located on the other cDNA strand 3' of the first unique site under conditions allowing the first and second primers to specifically hybridize with the first and second unique sequences, respectively, of the cDNA molecule encoding the PSA protein; (viii) contacting the composition of (vii) with DNA polymerase under conditions allowing the DNA polymerase to synthesis cDNA molecules encoding the PSA protein using the first or second primers to initiate synthesis and the heat denatured cDNA molecule encoding the PSA protein as a template; and (ix) repeating steps (vi) through (viii) for at least twenty five times; and detecting the presence of the cDNA molecule encoding the PSA protein and thereby determining the stage of prostate cancer.

As used herein, the phrase "specifically hybridizing" means the ability of a nucleic acid molecule to recognize a nucleic acid sequence complementary to its own and to form double-helical segments through hydrogen bonding between complementary base pairs. As used herein, a "unique sequence" is a sequence specific to only the nucleic acid molecules encoding the PSA protein.

The collection of blood from a patient is described in the Experimental Details. An adequate blood sample is 5–8 cc of peripheral blood. Although venous collection is discussed, peripheral blood can be drawn from arteries using methods known to one of skill in the art.

An example of one mRNA extraction procedure is provided in the Experimental Details, but the extraction of mRNA from a blood sample is well known to one of skill in the art and other methods can be used.

The preferred DNA polymerase is Taq Polymerase which is commercially available and has the additional benefit of retaining activity after exposure to DNA denaturing temperatures.

The determination that a human subject has PSA expressing cells circulating in the subjects peripheral blood can be made by detecting a cDNA product using the Method described hereinabove that consists of a base pair size predicted by the primers used and the known sequence of cDNA encoding the PSA protein. If primers other than those described in the Experimental Details are used, verification of the cDNA product produced should be done by sequencing the cDNA product.

This invention provides a method of determining the stage of prostate cancer in a human subject which comprises: collecting a sample of peripheral blood from a human subject; extracting mRNA molecules from the peripheral blood; amplifying a cDNA molecule encoding the PSA protein which comprises: (i) contacting the mRNA molecule extract with a nucleic acid molecule primer capable of specifically hybridizing to a nucleic acid sequence site included within the mRNA encoding the PSA protein under conditions allowing the primer to specifically hybridize to the mRNA encoding the PSA protein; (ii) contacting the composition of (i) with reverse transcriptase under conditions allowing the reverse transcriptase to transcribe a single stranded cDNA molecule copy of the mRNA molecule encoding the PSA protein; (iii) heat denaturing the cDNA and mRNA molecule of composition (ii); (iv) contacting the composition of (iii) with a first primer capable of specifically hybridizing to a first unique nucleic acid molecule sequence site located on the cDNA molecule complementary to the mRNA encoding the PSA protein under conditions allowing the first primer to specifically hybridize with the first unique nucleic acid molecule sequence site; (v) contacting the composition of (iv) with DNA polymerase under conditions allowing the DNA polymerase to synthesize a double stranded cDNA molecule encoding the PSA protein using the first primer to initiate synthesis and the single-stranded cDNA molecule as a template; (vi) heat denaturing the double-stranded cDNA molecule of composition (v); (vii) contacting the composition of (vi) with the first primer and a second nucleic acid molecule primer capable of specifically hybridizing with a second unique nucleic acid molecule sequence site wherein the second unique nucleic acid sequence site is located on the other cDNA strand 3' of the first unique site under conditions allowing the first and second primers to specifically hybridize with the first and second unique sequences, respectively, of the cDNA molecule encoding the PSA protein; (viii) contacting the composition of (vii) with DNA polymerase under conditions allowing the DNA polymerase to synthesis cDNA molecules encoding the PSA protein using the first or second primers to initiate synthesis and the heat denatured cDNA molecule encoding the PSA protein as a template; and (ix) repeating steps (vi) through (viii) for at least twenty five times; and detecting the presence of the cDNA molecule encoding the PSA protein which further comprises: loading the composition of step (ix) onto a gel; electrophoresing the cDNA into the gel with a DNA ladder; ethidium bromide staining the DNA inside the gel; visualizing the ethidium bromide stained DNA under ultraviolet light; and detecting the presence of the cDNA molecule encoding the PSA protein and thereby determining the stage of prostate cancer.

This invention provides a method of determining the stage of prostate cancer in a human subject which comprises: collecting a sample of peripheral blood from a human subject; extracting mRNA molecules from the peripheral blood; amplifying a cDNA molecule encoding the PSA protein which comprises: (i) contacting the mRNA molecule extract with a nucleic acid molecule primer capable of specifically hybridizing to a nucleic acid sequence site included within the mRNA encoding the PSA protein under conditions allowing the primer to specifically hybridize to the mRNA encoding the PSA protein; (ii) contacting the composition of (i) with reverse transcriptase under conditions allowing the reverse transcriptase to transcribe a single stranded cDNA molecule copy of the mRNA molecule encoding the PSA protein; (iii) heat denaturing the cDNA and mRNA molecule of composition (ii); (iv) contacting the composition of (iii) with a first primer capable of specifically hybridizing to a first unique nucleic acid molecule sequence site located on the cDNA molecule complementary to the mRNA encoding the PSA protein under conditions allowing the first primer to specifically hybridize with the first unique nucleic acid molecule sequence site; (v) contacting the composition of (iv) with DNA polymerase under conditions allowing the DNA polymerase to synthesize a double stranded cDNA molecule encoding the PSA protein using the first primer to initiate synthesis and the single-stranded cDNA molecule as a template; (vi) heat denaturing the double-stranded cDNA molecule of composition (v); (vii) contacting the composition of (vi) with the first primer and a second nucleic acid molecule primer capable of specifically hybridizing with a second unique nucleic acid molecule sequence site wherein the second unique nucleic acid sequence site is located on the other cDNA strand 3' of the first unique site under conditions allowing the first and second primers to specifically hybridize with the first and second unique sequences, respectively, of the cDNA molecule encoding the PSA protein; (viii) contacting the composition of (vii) with DNA polymerase under conditions allowing the DNA polymerase to synthesis cDNA molecules encoding the PSA protein using the first or second primers to initiate synthesis and the heat denatured cDNA molecule encoding the PSA protein as a template; and (ix) repeating steps (vi) through (viii) for at least twenty five times; and detecting the presence of the cDNA molecule encoding the PSA protein which comprises: adding digoxigenin-labeled nucleotides in step (iv); loading the composition of step (ix) which contains digoxigenin-labeled nucleotides onto a gel; electrophoresing the cDNA into the gel with a digoxigenin-labeled DNA ladder; transferring and fixing the DNA in the gel onto a membrane; contacting the DNA on the gel with an antibody which specifically binds digoxigenin, wherein the antibody is linked to an enzyme capable of directly or indirectly activating a chemiluminescent substrate; contacting the antibody bound DNA with the activatable chemiluminescent substrate; visualizing the presence of labeled DNA by exposing the membrane to a light sensitive device; and detecting the presence of the cDNA molecule encoding the PSA protein and thereby determining the stage of prostate cancer.

A preferred embodiment of the method to determining the stage of prostate cancer in a human subject comprises an enzyme capable of activating a chemiluminescent substrate which may be alkaline phosphatase, a the chemiluminescent substrate which may be 4-methoxy-4-(3-phosphate-phenyl)-spiro(1,2-dioxetane-3,2-adamantane) disodium salt, and a light sensitive device which may be X-ray film. Other light sensitive devices are known to those of skill in the art for recording labeled nucleotides (whether they be digoxigenin or radioactively labeled).

This invention provides a method of determining the stage of prostate cancer in a human subject which comprises: collecting a sample of peripheral blood from a human subject; extracting mRNA molecules from the peripheral blood; amplifying a cDNA molecule encoding the PSA protein which comprises: (i) contacting the mRNA molecule extract with a nucleic acid molecule primer capable of specifically hybridizing to a nucleic acid sequence site included within the mRNA encoding the PSA protein under conditions allowing the primer to specifically hybridize to the mRNA encoding the PSA protein; (ii) contacting the composition of (i) with reverse transcriptase under conditions allowing the reverse transcriptase to transcribe a single stranded cDNA molecule copy of the mRNA molecule encoding the PSA protein; (iii) heat denaturing the cDNA and mRNA molecule of composition (ii); (iv) contacting the composition of (iii) with a first primer capable of specifically hybridizing to a first unique nucleic acid molecule sequence site located on the cDNA molecule complementary to the mRNA encoding the PSA protein under conditions allowing the first primer to specifically hybridize with the first unique nucleic acid molecule sequence site, wherein the first primer comprises a nucleic acid molecule sequence of at least 15 nucleic acids that is the same or substantially the same as the nucleic acid sequence shown in FIG. 6; (v) contacting the composition of (iv) with DNA polymerase under conditions allowing the DNA polymerase to synthesize a double stranded cDNA molecule encoding the PSA protein using the first primer to initiate synthesis and the single-stranded cDNA molecule as a template; (vi) heat denaturing the double-stranded cDNA molecule of composition (v); (vii) contacting the composition of (vi) with the first primer and a second nucleic acid molecule primer capable of specifically hybridizing with a second unique nucleic acid molecule sequence site wherein the second unique nucleic acid sequence site is located on the other cDNA strand 3' of the first unique site under conditions allowing the first and second primers to specifically hybridize with the first and second unique sequences, respectively, of the cDNA molecule encoding the PSA protein; (viii) contacting the composition of (vii) with DNA polymerase under conditions allowing the DNA polymerase to synthesis cDNA molecules encoding the PSA protein using the first or second primers to initiate synthesis and the heat denatured cDNA molecule encoding the PSA protein as a template; and (ix) repeating steps (vi) through (viii) for at least twenty five times; and detecting the presence of the cDNA molecule encoding the PSA protein and thereby determining the stage of prostate cancer.

This invention provides a method of determining the stage of prostate cancer in a human subject which comprises: collecting a sample of peripheral blood from a human subject; extracting mRNA molecules from the peripheral blood; amplifying a cDNA molecule encoding the PSA protein which comprises: (i) contacting the mRNA molecule extract with a nucleic acid molecule primer capable of specifically hybridizing to a nucleic acid sequence site included within the mRNA encoding the PSA protein under conditions allowing the primer to specifically hybridize to the mRNA encoding the PSA protein; (ii) contacting the composition of (i) with reverse transcriptase under conditions allowing the reverse transcriptase to transcribe a single stranded cDNA molecule copy of the mRNA molecule encoding the PSA protein; (iii) heat denaturing the cDNA and mRNA molecule of composition (ii); (iv) contacting the composition of (iii) with a first primer capable of specifically hybridizing to a first unique nucleic acid molecule sequence site located on the cDNA molecule complementary to the mRNA encoding the PSA protein under conditions allowing the first primer to specifically hybridize with the first unique nucleic acid molecule sequence site; (v) contacting the composition of (iv) with DNA polymerase under conditions allowing the DNA polymerase to synthesize a double stranded cDNA molecule encoding the PSA protein using the first primer to initiate synthesis and the single-stranded cDNA molecule as a template; (vi) heat denaturing the double-stranded cDNA molecule of composition (v); (vii) contacting the composition of (vi) with the first primer and a second nucleic acid molecule primer capable of specifically hybridizing with a second unique nucleic acid molecule sequence site wherein the second unique nucleic acid sequence site is located on the other cDNA strand 3' of the first unique site under conditions allowing the first and second primers to specifically hybridize with the first and second unique sequences, respectively, of the cDNA molecule encoding the PSA protein, and wherein the second primer comprises a nucleic acid molecule sequence of at least 15 nucleic acids that is complementary to a nucleic acid molecule sequence that is the same or substantially the same as the nucleic acid sequence shown in FIG. 6; (viii) contacting the composition of (vii) with DNA polymerase under conditions allowing the DNA polymerase to synthesis cDNA molecules encoding the PSA protein using the first or second primers to initiate synthesis and the heat denatured cDNA molecule encoding the PSA protein as a template; and (ix) repeating steps (vi) through (viii) for at least twenty five times; and detecting the presence of the cDNA molecule encoding the PSA protein and thereby determining the stage of prostate cancer.

This invention provides a method of determining the stage of prostate cancer in a human subject which comprises: collecting a sample of peripheral blood from a human subject; extracting mRNA molecules from the peripheral blood; amplifying a cDNA molecule encoding the PSA protein which comprises: (i) contacting the mRNA molecule extract with a nucleic acid molecule primer capable of specifically hybridizing to a nucleic acid sequence site included within the mRNA encoding the PSA protein under conditions allowing the primer to specifically hybridize to the mRNA encoding the PSA protein; (ii) contacting the composition of (i) with reverse transcriptase under conditions allowing the reverse transcriptase to transcribe a single stranded cDNA molecule copy of the mRNA molecule encoding the PSA protein; (iii) heat denaturing the cDNA and mRNA molecule of composition (ii); (iv) contacting the composition of (iii) with a first synthesized oligonucleotide primer capable of specifically hybridizing to a first unique nucleic acid molecule sequence site located on the cDNA molecule complementary to the mRNA encoding the PSA protein under conditions allowing the first primer to specifically hybridize with the first unique nucleic acid molecule sequence site; (v) contacting the composition of (iv) with DNA polymerase under conditions allowing the DNA polymerase to synthesize a double stranded cDNA molecule encoding the PSA protein using the first primer to initiate synthesis and the single-stranded cDNA molecule as a template; (vi) heat denaturing the double-stranded cDNA molecule of composition (v); (vii) contacting the composition of (vi) with the first primer and a second synthesized oligonucleotide primer capable of specifically hybridizing with a second unique nucleic acid molecule sequence site wherein the second unique nucleic acid sequence site is located on the other cDNA strand 3' of the first unique site under conditions allowing the first and second primers to specifically hybridize with the first and second unique sequences, respectively, of the cDNA molecule encoding the PSA protein; (viii) contacting the composition of (vii) with DNA polymerase under conditions allowing the DNA polymerase to synthesis cDNA molecules encoding the PSA protein using the first or second primers to initiate synthesis and the heat denatured cDNA molecule encoding the PSA protein as a template; and (ix) repeating steps (vi) through (viii) for at least twenty five times; and detecting the presence of the cDNA molecule encoding the PSA protein and thereby determining the stage of prostate cancer.

The preferred embodiment of the first synthesized oligonucleotide primer is a synthesized oligonucleotide primer comprising a nucleic acid molecule with a nucleotide sequence of 5'-GATGACTCCAGCCACGACCT-3'. (SEQ. ID. NO:4)

The preferred embodiment of the second synthesized oligonucleotide primer is a synthesized oligonucleotide primer comprising a nucleic acid molecule with a nucleotide sequence of 5'-CACAGACACCCCATCCTATC-3'. (SEQ. ID. NO:3)

The most preferred embodiment of first and second nucleic acid molecule primers is a first primer with a nucleotide sequence of 5'-GATGACTCCAGCCACGACCT-3'(SEQ. ID. NO:4), and a second nucleic acid molecule primer with a nucleotide sequence of 5'-CACAGACACCCCATCCTATC-3'(SEQ. ID. NO:3), wherein the use of these two primers in the hereinabove disclosed methods for determining the stage of prostate cancer in a human subject produces an amplified cDNA which is 710 base pairs long.

This invention provides a method of determining the stage of prostate cancer in a human subject which comprises: collecting a sample of peripheral blood from a human subject; extracting mRNA molecules from the peripheral blood; amplifying a cDNA molecule encoding the PSA protein which comprises: (i) contacting the mRNA molecule extract with a nucleic acid molecule primer capable of specifically hybridizing to a nucleic acid sequence site included within the mRNA encoding the PSA protein under conditions allowing the primer to specifically hybridize to the mRNA encoding the PSA protein, wherein the primer capable of specifically hybridizing the mRNA encoding the PSA protein is an oligo(dT)$_N$ primer; (ii) contacting the composition of (i) with reverse transcriptase under conditions allowing the reverse transcriptase to transcribe a single stranded cDNA molecule copy of the mRNA molecule encoding the PSA protein; (iii) heat denaturing the cDNA and mRNA molecule of composition (ii); (iv) contacting the composition of (iii) with a first primer capable of specifically hybridizing to a first unique nucleic acid molecule sequence site located on the cDNA molecule complementary to the mRNA encoding the PSA protein under conditions allowing the first primer to specifically hybridize with the first unique nucleic acid molecule sequence site; (v) contacting the composition of (iv) with DNA polymerase under conditions allowing the DNA polymerase to synthesize a double stranded cDNA molecule encoding the PSA protein using the first primer to initiate synthesis and the single-stranded cDNA molecule as a template; (vi) heat denaturing the double-stranded cDNA molecule of composition (v); (vii)

contacting the composition of (vi) with the first primer and a second nucleic acid molecule primer capable of specifically hybridizing with a second unique nucleic acid molecule sequence site wherein the second unique nucleic acid sequence site is located on the other cDNA strand 3' of the first unique site under conditions allowing the first and second primers to specifically hybridize with the first and second unique sequences, respectively, of the cDNA molecule encoding the PSA protein; (viii) contacting the composition of (vii) with DNA polymerase under conditions allowing the DNA polymerase to synthesis cDNA molecules encoding the PSA protein using the first or second primers to initiate synthesis and the heat denatured cDNA molecule encoding the PSA protein as a template; and (ix) repeating steps (vi) through (viii) for at least twenty five times; and detecting the presence of the cDNA molecule encoding the PSA protein and thereby determining the stage of prostate cancer.

As used herein a oligo(dT)$_N$ primer is an oligonucleotide primer consisting of sequence of thymidine base pairs where N equals 12–18.

This invention provides a method of determining the stage of prostate cancer in a human subject which comprises: collecting a sample of peripheral blood from a human subject, wherein the peripheral blood contains PSA expressing cells at a concentration equal to or greater than one PSA expressing cell per 100,000 blood cells; extracting mRNA molecules from the peripheral blood; amplifying a cDNA molecule encoding the PSA protein which comprises: (i) contacting the mRNA molecule extract with a nucleic acid molecule primer capable of specifically hybridizing to a nucleic acid sequence site included within the mRNA encoding the PSA protein under conditions allowing the primer to specifically hybridize to the mRNA encoding the PSA protein; (ii) contacting the composition of (i) with reverse transcriptase under conditions allowing the reverse transcriptase to transcribe a single stranded cDNA molecule copy of the mRNA molecule encoding the PSA protein; (iii) heat denaturing the cDNA and mRNA molecule of composition (ii); (iv) contacting the composition of (iii) with a first primer capable of specifically hybridizing to a first unique nucleic acid molecule sequence site located on the cDNA molecule complementary to the mRNA encoding the PSA protein under conditions allowing the first primer to specifically hybridize with the first unique nucleic acid molecule sequence site; (v) contacting the composition of (iv) with DNA polymerase under conditions allowing the DNA polymerase to synthesize a double stranded cDNA molecule encoding the PSA protein using the first primer to initiate synthesis and the single-stranded cDNA molecule as a template; (vi) heat denaturing the double-stranded cDNA molecule of composition (v); (vii) contacting the composition of (vi) with the first primer and a second nucleic acid molecule primer capable of specifically hybridizing with a second unique nucleic acid molecule sequence site wherein the second unique nucleic acid sequence site is located on the other cDNA strand 3' of the first unique site under conditions allowing the first and second primers to specifically hybridize with the first and second unique sequences, respectively, of the cDNA molecule encoding the PSA protein; (viii) contacting the composition of (vii) with DNA polymerase under conditions allowing the DNA polymerase to synthesis cDNA molecules encoding the PSA protein using the first or second primers to initiate synthesis and the heat denatured cDNA molecule encoding the PSA protein as a template; and (ix) repeating steps (vi) through (viii) for at least twenty five times; and detecting the presence of the cDNA molecule encoding the PSA protein and thereby determining the stage of prostate cancer.

Experimentail Details

Human Materials and Patient Selection

Two groups of prostate cancer patients were examined during our study; Group 1 comprised 10 patients with untreated metastatic prostate cancers (T4) confirmed by markedly elevated PSA values and the detection of metastatic lesions on a bone scan. Group 2 consisted of 48 patients with clinically localized prostate cancer (T1-T2c) who were scheduled for radical retropubic prostatectomy. All of these patients had received a digital rectal examination and a serum PSA determination (Hybritech Inc., San Diego, Calif.) as well as a bone scan prior to surgery. In each case a CT scan and/or endorectal coil MRI was used for local staging of the tumor. Nine of the patients from group 2 received preoperative treatment with flutamide (750 mg/day) as a means to reduce bulky tumor mass prior to surgery. All physical examinations and surgical procedures for the patients in group 2 were performed by a single surgeon (CAO).

In addition to the prostate cancer patients, three groups of non-prostate cancer controls were analyzed: Group 1 comprised 20 females hospitalized at our institution, Group 2 consisted of 20 young males (ages 19–49) with no prior urological disease history, and Group 3 consisted of 25 age-matched males (ages 45–77, mean 62) that were under outpatient treatment for BPH. The age-matched control male patients all had serum PSA values less than 4.0 and negative digital rectal examinations. All patients and controls were evaluated at our institution, and their participation in this study was approved by the Internal Review Board.

Patient Samples

Venous blood (5 cc) was collected from each individual in EDTA-treated collection tubes, placed immediately on ice, and processed within 3 hours of phlebotomy. For surgical candidates, the samples were obtained usually 1 week prior to surgery, at least two weeks from digital rectal examination and two weeks from prostate needle biopsy. Samples were diluted with an equal volume of phosphate-buffered saline (PBS) and carefully layered onto 8 cc of Ficoll-Pack (Pharmacia Inc., Piscataway, N.J.). The sample was centrifuged at 400×g for 20 min., and the buffy coat cells were recovered. The cells were washed in 50 cc PBS and were re-centrifuged at 1000×g for 30 min to produce a cell pellet.

A surgical specimen containing human prostate cancer was obtained from the human tumor bank operated by the Department of Pathology at this institution. This tissue was excised from a radical prostatectomy specimen and was frozen in liquid nitrogen and stored at −90° C.

Cell Culture

The human PSA-expression LnCaP cell line was originally established from a patient with metastatic prostate cancer to the pelvic lymph nodes (11). Monolayer propagation of these cells was in RPMI media supplemented with 5% Fetal Bovine Serum (FBS), 100 units/ml of penicillin and 0.1 mg/ml streptomycin. Every 2 days the cells received fresh medium and confluent cultures were dispersed with trypsin (0.05%):EDTA (0.02%) solution for subsequent passage. Serial dilutions of trypsinized cells were made in PBS to achieve cell densities as follows: 10,000 cells per ml, 1000 cells per ml, 100 cells per ml, and 100 cells per ml. These dilutions were added to $10^6$ cultured immortalized B-cells (gift of R. Dalla Favera, Columbia University), centrifuged at 1500 rpm for 5 min., and prepared for RNA extraction.

RNA Extraction

Total RNA was obtained from these cells by a modification of the Guanididium thiocyanate/phenol/chloroform extraction technique (12) utilizing the RNAzole B reagent of Tel-Test, Inc., (Friendswood, Tex.). The RNA pellet obtained after ethanol/sodium acetate precipitation was dried under vacuum and dissolved in 50 $\mu$l of RNase-free water. Quantification of RNA was done based on spectrophotometric measurements at 260 nm.

Reverse Transcription Reaction

An aliquot containing 1 $\mu$g of total RNA was added to 0.5 $\mu$g of oligo(dT)$_{12-18}$ primer (Gibco, BRL, Life Technologies, Inc.(, and brought to a final volume of 20 $\mu$l. The samples were placed at 65° C. for 5 min., then chilled on ice for 5 min. The primer annealed RNA was added to 30 $\mu$l master reaction mixture so that the final concentration of the following components were achieved: 1 mM of each dNTP, 50 mM Tris-HCl (ph 8.3), 75 mM KCl, 3 mM MgCl$_2$, 10 mM DTT, 10 units per reaction of Placental RNase inhibitor, and 200 units per reaction of M-MuLV Reverse Transcriptase (Superscript II, Gibco BRL). The reaction was incubated at 42° C. for 15 min. and the enzyme was heat inactivated at 95° C. for 15 seconds.

Polymerase Chain Reaction (PCR)

Oligonucleotide primers, specific for the human PSA cDNA coding region, were designed with the aid of the primer analysis software, OLIGO (version 4.0, National Biosciences, Plymouth, Minn.) and were synthesized by national Biosciences. The 18-base pair primers were designed to span across three exons; from exon 3 and extending into exon 5 with the following sequences:

PSA3':5'-CACAGACACCCCATCCTATC-3' (SEQ. ID. NO:3)

PSA5':5'-GATGACTCCAGCCACGACCT-3' (SEQ. ID. NO:4) oligonucleotide primers for human glyceraldehyde 3-phosphate dehydrogenase (G3PDH) were obtained from Clontech laboratories (Palo Alto, Calif.) and PCR for this gene produce was performed in a separate reaction for each sample. The PCR reaction was done in a total volume of $\mu$l containing one fifth of the RT reaction with a final concentration of the following reagents: 20 mM Tris-HCl (ph 8.3 at 20° C.), 50 mM Kcl, 1.5 mM MgCl$_2$, 0.2 mM of each dNTP, 2.5 units of Taq Polymerase and 10 pmoles of each primer. When enhanced sensitivity was desired, digoxigenin-11-deoxyUrdine Triphosphate (Dig-dUTP) (Boehringer Mannheim Corp., Indianapolis, Ind.) was added to a final concentration of 0.55 $\mu$M. All reactions were prepared with sets of PCR-dedicated micropipettors using plugged tips to protect against cross contamination.

A total of 35 cycles were completed with the following specification: A) cycle 1, 95° C. (4 min); B) cycles 2–16, 95° C. (1 min), 60° C. (1 min), 72° C. (1 min); D) cycles 28–24, 95° C. 1 min, 60° C. 1 min., 72° C. 2 min, and the last cycle was at 72° C. for 15 min. With the addition of Dig-dUTP in the PCR reaction the number of cycles was decreased to 25 with the removal of cycle set C. The PCR products were stored at 4° C. until electrophoresis. Aliquots of the reaction were electrophoresed on 2.5% agarose gels in TEA buffer at 80 V. The gels were stained with ethidium bromide and were viewed under UV light.

Cloning of the PSA-PCR Product

The 710 base pair band representing the PCR produce derived from a human prostate tumor was excised and purified from a 2.0% agarose gel. This PCR product was ligated into the PCR cloning site of the pCR II vector (Invitrogen Corp.,(. The cloned insert was sequenced using SP6 and T7 primers by dideoxy-nucleotide sequence analy-sis (13). The sequence obtained for this DNA insert was compared with the Human PSA genomic sequence of Klobeck, et al. (14) obtained in the Genebank (Accession #Xl4810).

Enhanced PCR Detection

Digoxigenin-enhanced detection of the PSA PCR reaction product was accomplished with the use of Genius DNA labeling kit (Boehringer Mannhein) with modifications. Southern blotting of the gel fractionated PCR reaction onto positively charged nylon membranes (Boehringer Mannheim) was accomplished following standard techniques (15) and was fixed onto the membrane by UV exposure. Membrane washing and blocking was according the manufacture's specifications. Alkaline phosphatase-conjugated anti-digoxigenin antibody (Fab fragment) was used at a 1:50,000 dilution in Genius 2 buffer (2% blocking agent in 100 mM Tris-HCl (ph 7.5 at 20° C.), 150 mM NaCl prior to incubation with the membrane. The chemiluminescent substrate, Lumi-Phos 530 [0.33 mM Lumigen PPD [4-methoxy-4-(3-phosphate-pphenyl)-sprio (1,2-dioxetane-3,2-adamantane) disodium salt]; 0.88 mM MgCL$_2$; 1.13 mM cetyltrimethy-ammonium bromide; 0.035 mM fluorescein surfactant], was diluted 1:1 in 100 mM Tris-HCL (pH 9.5 at 20° C.), 100 mM NaCl, 50 mM MgCL$_2$ and a small amount was carefully spread across the membrane. The wrapped membrane was exposed to X-ray film, typically, for only several minutes and the film was developed.

Statistical Methods

Logistic regression analysis was used to determine the statistical significance of each of the following preoperative factors: PSA, PSAD, imaging (CT-scan and/or endorectal MRI), and PCR. A Chi-square score was determined for each independent variable to evaluate the likelihood of predicting margin positive-disease. In addition, preoperative factors were examined with and without the PCR assay to determine if deletion or addition of assay results would add to the prediction of margin positive disease.

Results

Detection of PSA-Synthesizing Cells by PCR

RNA was extracted from the LNCaP cell line and from a surgically-removed specimen containing prostate cancer. This RNA was reverse transcribed to cDNA and then utilized in a PCR reaction with primers designed to amplify a 710 bp DNA fragment from human PSA RNA. Following electrophoresis of the PCR products, we were able to identify the appropriate DNA fragment corresponding to PSA only in reactions containing cDNA (FIG. 1). This 710 bp fragment was cloned into a plasmid vector and was sequenced. The sequence of the insert (not shown here) corresponded at every nucleotide to the sequence of human PSA appearing in the genebank.

PCR of LnCaP Dilution

Figure 2B:
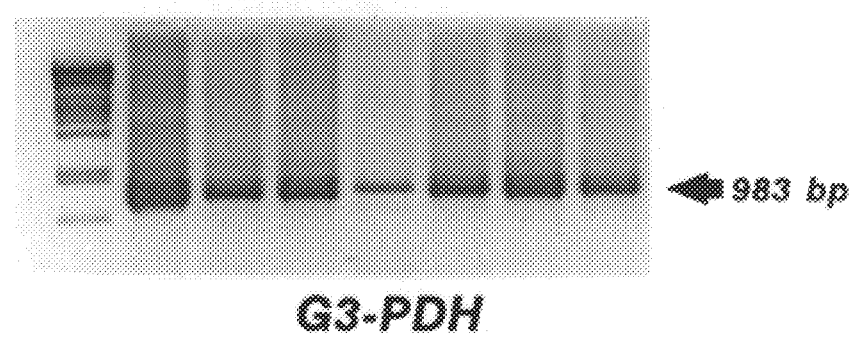
Figure 3A:
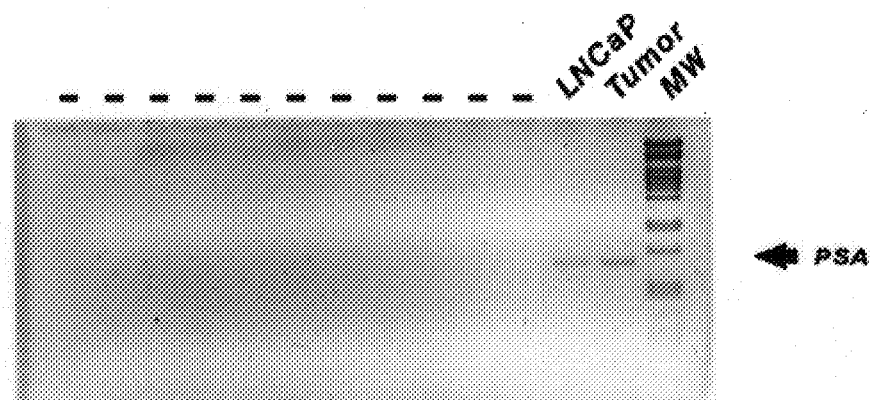
FIGS. 3A and 3B Inability to detect PSA synthesizing cells in peripheral blood lymphocytes of noncancer male patients. Total RNA was extracted from the lymphocyte fraction of 8 young males with no history of urological disease and age-matched BPH patients. These RNAs were assayed by RT-PCR with PSA primers. None of these specimens yielded a positive fragment by ethidium bromide visualization (FIG. 3A) or by the enhanced visualization method (not shown). All specimens did yield an appropriate reaction product when G3PDH primers were utilized in the PCR reaction.
Figure 3B:
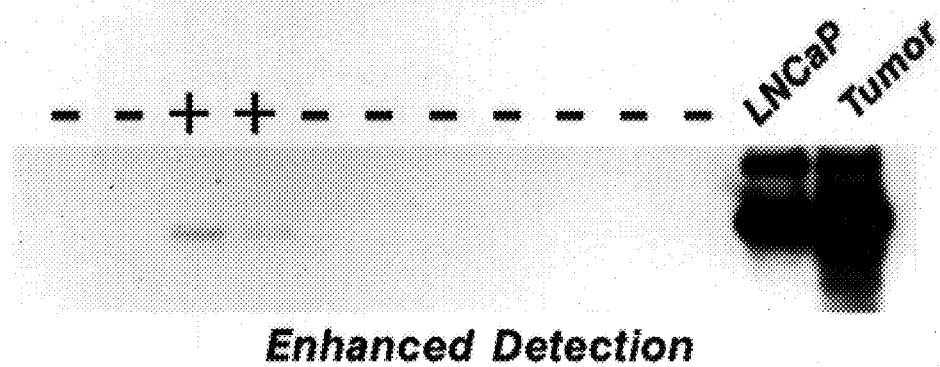
Figure 4A:
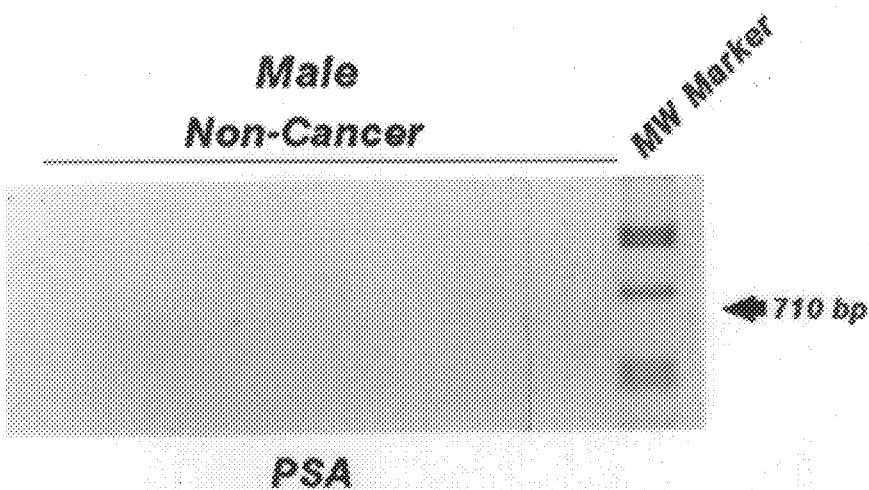
FIGS 4A and 4B Inability to detect PSA synthesizing cells in peripheral blood lymphocytes of females. Total RNA was extracted from the lymphocyte fraction of 6 females. These RNAs were assayed by RT-PCR using PSA primers. None of these specimens yielded a positive fragment by ethidium bromide visualization (FIG. 4A) or by the enhanced method (now shown). All specimens did yield an appropriate reaction product when G3PDH primers were utilized in the PCR reaction (FIG. 4B).
Figure 4B:
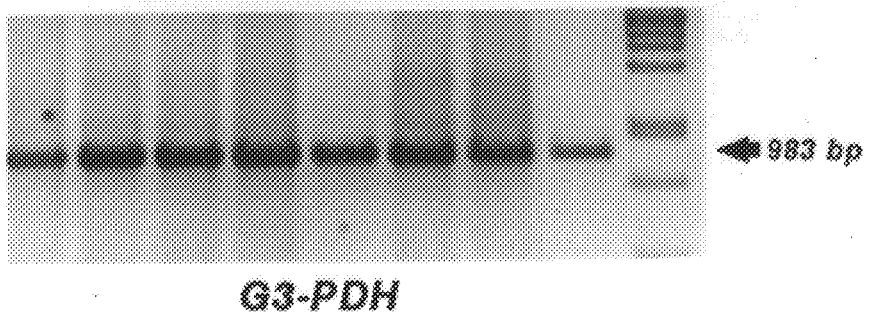

By diluting known quantities of LnCaP cells into cultured B-lymphocytes, were able to evaluate the minimum number of PSA-synthesizing cells detectable by PCR. Serial dilutions of LNCaP cells were added to aliquots containing $10^6$ human B-lymphocytes. RNA was extracted from these diluted specimens and was assayed in individual reactions by RT-PCR. A portion of the reaction product was electrophoresed on an agarose gel and, as shown in FIGS. 2A and 2B, when the reaction included primers for human PSA, we could detect as few as 10 PSA-synthesizing cells (1 in 100,000). Duplicate aliquots of cDNA from each of these specimens were also run for PCR using primers for human G3PDH, and, in contrast to the reactions with human PSA primers, in which the sample lacking LNCaP cells failed to give a reaction product, all specimens yielded the expected 983 bp G3PDH DNA fragment (FIGS. 2A and 2B). All subsequent reactions on patient specimens were carried out so that each cDNA had a duplicate reaction containing G3PDH primers as a positive control for cDNA integrity. Each subsequent PCR experiment involving patient samples included one specimen of LNCaP cDNA to serve as a positive control reaction for PSA detection. In addition, a sample having no added cDNA was included among the specimen set to provide a negative control and to ensure against contamination of PCR reagents.

PCR analysis on Bloods From Control Patients

PCR analysis was performed on the RNA extracted from venous blood lymphocytes obtained from 20 male subjects (ages 19–41), and 20 female patients (ages 23–76). None of these control specimens revealed a positive PCR reaction (FIGS. 3A–3B and FIGS. 4A–4B). In addition, lymphocyte fraction RNA of 25 age-matched BPH patients were analyzed to determine the possible effect of BPH on the PCR assay. None of these patients revealed a positive PCR fragment as assessed by ethidium bromide staining of the agarose gel following electrophoresis. The addition of digoxigenin-dUTP to the PCR reaction enabled us to increase the sensitivity of detection of the PSA-PCR fragment as described in more detail for our prostate cancer patients. The enhanced method of detection was performed on each of these groups of patients, and the 710 bp PSA DNA fragment was not detected in any specimen (not shown).

PCR analysis of Bloods from Metastatic Prostate Cancer Patients

Ten patients with confirmed but untreated metastatic prostate cancer were analyzed by the RT-PCR assay. All patients in this category had positive bone scans indicating the presence of bony metastases. PSA values for patients in this group ranged from 42 to 412 ng/ml. The peripheral lymphocyte RNA RT-PCR assay for 8 of these 10 patients revealed the presence of the 710 bp PSA PCR fragment. Five of these positives were revealed by ethidium bromide visualization and 3 additional specimens were revealed by the enhanced method for detection (not shown here).

PCR Analysis on Bloods from Localized Prostate Cancer Patients

Figures 5A, 5B:
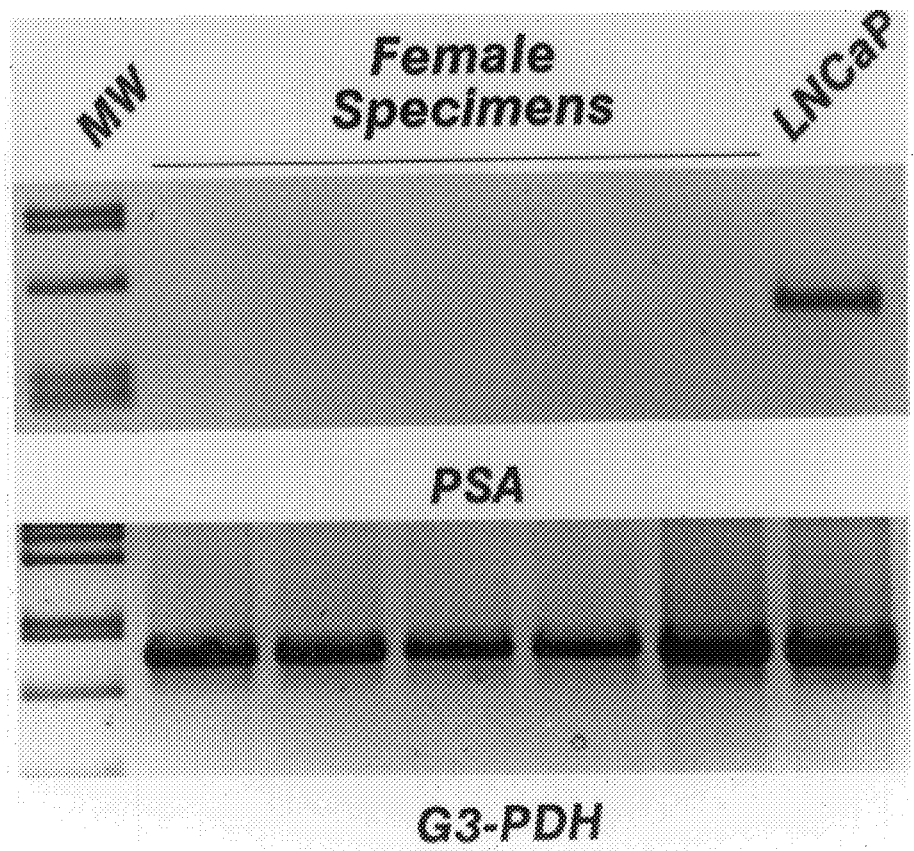
FIGS. 5A and 5B Comparison of RT-PCR and enhanced RT-PCR for detection of PSA-synthesizing cells in the peripheral blood of 23 individual prostate cancer patients.

Lymphocyte fraction RNAs from a total of 48 patients with clinically confined prostate cancer were analyzed by RT-PCR for PSA. Only 4 of these patients were positive for the PSA-PCR reaction by ethidium bromide staining analysis following agarose gel electrophoresis. However, an additional 7 patients were found to be positive with the use of the enhanced method of detection (FIG. 5, A and B), bringing the total to 11 (or 22.9% of patients in this category). The radical prostatectomy specimens obtained from these patients were subsequently analyzed as to the status of the Gleason grade of the tumor; whether the tumor extended into the prostatic capsule (capsular penetration); the presence of tumor at the surgical margins; and seminal vesicle involvement. None of these patients had detectable metastasis to the pelvic lymph nodes.

Table 1 summarizes the correlation of the patient PCR analysis with respect to pathological tumor stage. In the 48 patients operated for clinically localized prostate cancer, 15 (31.2%) were subsequently found to have tumor penetrating the prostatic capsule. Of these 15 patients, an RT-PCR fragment for PSA was amplified from 11 of the blood specimens. Therefore, if the RT-PCR blood assay was utilized as a means to discriminate prostate cancer patients with only capsular invasion from this population, it would have a sensitivity of 73% and a specificity of 89%.

Ten of the 48 patients were subsequently found to have tumor present at the surgical margin (20.8% of surgical patient population). Nine of these 10 margin positive patients were also positive for PSA by RT-PCR. We calculated the sensitivity and specificity of the PCR assay for detecting margin positive disease in this patient population at 90% and 94%, respectively. Based on our statistical analysis, the RT-PCR assay is a

TABLE 1

Comparison of PCR findings in 48 patients with clinically localized prostate cancers and final pathological stage. Sensitivity, specificity, and predictive values were calculated for PCR in each category of pathology.

|  | POSITIVE MARGINS | CAPSULAR PENETRATION | POSITIVE SEMINAL VESICLE |
|---|---|---|---|
| Number of Patients | 10/48 (20.8%) | 15/48 (31.2%) | 2/48 (4.16%) |
| PCR+ | 9 | 11 | 1 |
| Sensitivity | 90% | 73% | 50% |
| Specificity | 94% | 89.2% | 75.6% |
| Positive Predictive Value | 82% | 78% | 78% |
| Negative Predictive Value | 93*% | 61% | 18% | strong predictor of tumor spread through and beyond the prostatic capsule. An odds ration analysis of this 48 patient sample (patient group 2) estimating the likelihood that the presence of tumor at the surgical margin would be associated with a positive PCR assay was 162 (95% confidence limits: 13.1 to 1991.6), respectively. Finally, 2(4.16%) of the 48 surgical patients were found to have tumor invading the seminal vesicle. The PCR assay had a 50% sensitivity and 75.6% specificity for detecting patients with disease into the seminal vesicles. However, there were only 2 patients in the study with positive seminal vesicles, therefore, no good statistical correlation could be determined for this subgroup of patients. Used as an independent variable to predict prostate cancer confined to the prostate gland, RT-PCR for PSA had a positive predictive value of 81.8%.

The staging results predicted by preoperative imaging modalities were statistically compared to the results obtained with PCR. Prior to surgery, all patients had a serum PSA obtained and DRE by performed by one examiner (CAO). Patients either had a CT-scan of the pelvis, an endorectal coil MRI, or both to detect extraprostatic disease. Imaging sensitivity and specificity for disease confined to the prostate is listed in Table 2 and compared to the results of the RE-PCR assay. RT-PCR revealed the highest overall sensitivity for detecting extraporstatic tumor (73%).

Additionally, a stepwise logistic regression analysis was performed to identify the single variable (PSA, PSAD, CT scan, endorectal MRI or PCR) which would predict cancer at the surgical margin. The RT-PCR assay had the highest Chi-square score ($\chi^2$=25.3p>0.0001) for this distinction (Table 2). In fact, RT-PCR proved to be the only variable which met a

TABLE 2

Comparison of PCR to standard pre-operative staging modalities in 48 patients undergoing radical prostatectomy. PCR was found to have the highest sensitivity and predictor of confined prostate cancer (negative predictive value).

|  | PCR | DRE | CT SCAN | ENDORECTAL COIL MRI |
|---|---|---|---|---|
| TRUE (+) | 11 | 2 | 2 | 1 |
| TRUE (−) | 32 | 37 | 28 | 3 |
| FALSE (+) | 0 | 0 | 5 | 1 |
| FALSE (−) | 5 | 9 | 6 | 3 |
| SENSITIVITY TP/TP + FN | 68.7% | 18% | 25% | 25% |
| SPECIFICITY TN/TN + FP | 100% | 100% | 84.8% | 75% | confidence level of 95%. Prostate specific antigen density (PSAD) is defined as a unitless ratio combining the value of the serum PSA measurement with the prostate volume. PSAD has been previously shown to be useful predictor for distinguishing benign from malignant prostate tissue (16). The mean PSAD was 0.29 in our surgical patient population with a standard deviation of 0.25. Table 3 compares the PSAD to the pathological stage for these patients. In this series, PSAD as a single predictor of margin positive disease was second best to RT-PCR. Stepwise logarithmic analysis of PSAD for this group of patients revealed a Chi-square score of 11.0, p>.0009. Simple serum PSA values are compared to the final pathological stage in Table 4. The majority of patients (54%) had PSA values in the 4 to 10 ng/ml range. The mean PSA value for all patients was 11.2 ng/ml (S.D. ±7.9). The Chi-square score for PSA as a single-modality predictor of extraprostatic disease was calculated to be $\chi^2=7.09 p>0.0001$. Only 2 patients had PSA values greater than 30. Both of these patients were found to have positive surgical margins and were also PCR positive.

It is of further interest that 9 of the 48 radical prostatectomy patients had received flutamide therapy prior to their surgery and prior to the phlebotomy from which the PSA-PCR assay was performed. This subset of patients included 2 which had a positive PCR reaction and 7 which were negative. Cochran-Mantel-Haenszel summary odds ratio analysis controlling for patients given flutamide therapy resulted in an adjusted odds ration of 69.7 (95% confidence limits: 6.6 to 725.6). Furthermore, removal of these flutamide-treated patients from the rest of the surgical patients did not affect the strong correlation between positivity on the PCR assay and the presence of tumor at the surgical

TABLE 3

Correlation of PSAD and pathological stage in 48 patients with clinically localized cancer of the prostate.

| PSAD | NUMBER OF PATIENTS | +PCR | POSITIVE MARGINS | POSITIVE CAPSULE | POSITIVE SEMINAL VESICLE |
|---|---|---|---|---|---|
| 0–0.15 | 10 | 1(10%) | 1(10%) | 1(10%) | 0(0%) |
| 0.16–0.30 | 20 | 3(15%) | 2(10%) | 7(35%) | 0(0%) |
| 0.31–0.60 | 10 | 3(30%) | 2(20%) | 2(20%) | 1(10%) |
| >0.60 | 8 | 4(50%) | 5(63%) | 6(75%) | 1(12.5%) |
| TOTAL | 48(100%) | 11(22.9%) | 10(20.8%) | 15(31.2%) | 2(4.2%) |

TABLE 4

Correlation of serum PSA and pathological stage in 48 patients with clinically localized cancer of the prostate.

| PSA/(ng/ml) | NUMBER OF PATIENTS | +PCR | POSITIVE MARGINS | POSITIVE CAPSULE | POSITIVE SEMINAL VESICLE |
|---|---|---|---|---|---|
| 0–4.0 | 2 | 0(0%) | 0(0%) | 0(0%) | 0(0%) |
| 4.1–10.0 | 26 | 3(11.5%) | 3(11.5%) | 6(23%) | 0(0%) |
| 10.1–20 | 14 | 3(21.4%) | 3(21.4%) | 6(42.8%) | 0(0%) |
| 20.1–30 | 4 | 3(75%) | 2(50%) | 2(50%) | 2(50%) |
| 30.1–40 | 2 | 2(100%) | 2(100%) | 2(100%) | 0(0%) |
| Total | 48 | 11 | 10 | 16 | 2 | margin. With this change, the RT-PCR assay now had 100% sensitivity for identifying margin positive disease with a specificity of 93.5%.

Discussion

In this study, we have determined that the detection of blood-borne PSA-synthesizing cells by RT-PCR can be accomplished in patients with localized as well as metastatic prostate cancer and this detection provides a reliable marker for predicting local invasion of a prostate tumor prior to surgical procedures. PSA, a 34,000 kd glycoprotein, is a prostate-specific serine protease which is expressed exclusively by prostate epithelial cells, the cells most frequently involved in prostatic oncogenesis (17). In recent years, assays used to detect this protein in the blood have revolutionized the management of prostate cancer patients by allowing the earlier detection of prostate tumors as well as by providing a more effective means to follow the progression of the disease. As we have shown here, the specificity of PSA for prostate cells has further enabled the development of this RT-PCR based assay that can detect as few as 1 PSA-synthesizing cell in 100,000 blood cells. When this assay was applied to peripheral blood specimens taken from prostate cancer patients with confirmed metastases, it was positive for the overwhelming majority (80%) of patients in this category available for our study. The biological significance of these prostate cells in the circulation is not known at the present time. However, the high percentage of frank metastatic patients that give a positive reaction on this assay suggests that it is detecting circulating metastatic prostate cells. When this assay was applied to blood specimens taken from prostate cancer patients with suspected prostate-confined disease, it was positive only in a much smaller subset (22.9%) of these patients. Because the subset of patients detected by the PSA-PCR assay correlated strongly with local invasive spread of the cancer, the significance of this determination may lie in a more accurate measure of staging than with the imaging modalities utilized today (ie. MRI, bone scan and CT-scan). Statistical analysis of the data gathered in this survey supports the presumption that patients with localized prostate cancer that react positively on this assay represent a subset that are at increased risk for recurrent disease, despite surgical extirpation of the gland.

Two previous studies in the literature have addressed the concept of hematogenous dissemination of prostate cancer. Using flow cytometry, Hamdy et al. demonstrated that PSA-positive cells could be detected in 25 prostate cancer patients with bone metastasis while none of the control patients had PSA-positive cells in the peripheral blood (18). The results of this study were peculiar in the some patients had greater than 50% PSA-positive cells in the circulating lymphocyte fraction. However, a second report, describing the PCR amplification of a PSA DNA fragment from reverse transcribed peripheral blood RNA of metastatic prostate cancer patients confirmed its detection in 4 of 12 patients (33%) whereas it was never identified in a small group of control (non-cancer) patients (10). Our current investigation included 3 groups of non-cancer control patients and we never detected an appropriate PSA RT-PCR fragment from any blood specimen obtained from women, young males, or age-matched control males with benign enlargement of the prostate gland (total of 65 specimens). Therefore, as supported by the previous study (10) and by our current results, there is no evidence to date that non-prostate cancer patients have PSA-synthesizing cells present in the peripheral circulation. In contrast, untreated metastatic prostate cancer patients were overwhelmingly positive on this assay (80%). Moreover, the only other group that gave a positive reaction on this assay were a minority of patients (11 of 48 or 22.9%) with suspected clinically localized prostate cancer. Therefore, our results indicate that the blood-based RT-PCR assay for PSA is specific for prostate cancer patients.

In our series of patients with localized prostate cancer, 10 patients were found to have tumor at the surgical margin subsequent to their radical surgery. of these 10 patients, 9 had a positive RT-PCR reaction for PSA (90% sensitivity). Of the remaining 38 patients with margin negative disease, only 2 were found to have a positive PCR result (94% specificity). This is convincing evidence that a strong clinical correlation exists between the local extent of the tumor and hematogenous dissemination. In the patients with capsular penetration, the PCR assay was less sensitive than for margin positive disease (73%). Prostate cell dissemination into the circulation may therefore be a factor of the primary tumor volume. As tumor volume increases and encroaches on blood vessels, the basement membrane of endothelium may break down, allowing for tumor cells to enter the circulation. Interestingly, none of the patients in this group were found to have lymph node involvement, and all patients had negative bone scans, indicating that hematogenous dissemination may occur prior to lymphatic or bony involvement.

In this study, a fraction of the patients were given a course of flutamide therapy for "downstaging" of bulky tumors. Since 2 of these treated patients were positive on the PCR assay, it is clear that a short course of flutamide therapy does not abolish the ability of this PCR assay to detect circulating prostate cells. Considering that the only patient that had tumor at the surgical margin and remained unreactive on the assay was of this treatment group, allows for the possibility that flutamide treatment prior to phlebotomy may decrease the sensitivity of the PCR assay. However, the results of the Cochran-Mantel-Haenzszel summary odds ratio analysis controlling for flutamide-treated patients remained statistically significant, suggesting that flutamide does not meaningfully alter the sensitivity of the PSA-PCR assay.

The presence or absence of extracapsular prostate cancer is often the critical factor in therapeutic decisions regarding prostate cancer. Radical prostatectomy has been shown to be the most effective therapy when disease remains confined to the gland (19, 20). Microscopic disease that invades into the capsule or to the surgical margin significantly reduces the chance for cure. Several studies have shown that tumor can be detected at the surgical margin in 11 to 32% of clinical stage A patients and 23–71% of clinical stage B prostate cancer patients (21, 22). These high numbers directly reflect the inaccuracies of the current preoperative staging modalities. A recent report from a multi-institutional investigation comparing MRI and TRUS in the early staging of prostate cancer concluded that these modalities are not highly accurate because neither technique could identify microscopic spread (23). Eight patients in this current study had MRI with endorectal coils prior to surgery. This expensive modality was able to predict confined tumor in 50% of the cases. If the MRI was interpreted as positive, i.e. extracapsular, the MRI results were only 50% accurate. From a statistical standpoint, when PCR was compared to preoperative imaging, the PCR assay had the highest reliability (based on Chi-square analysis) in predicting margin positive disease.

The most common used imaging modality for local staging cancer is still the CT-scan, even though this modality traditionally understages a significant number of patients. From the perspective of prognostic ability and cost effectiveness perspective CT scanning is under serious investigation (24). Review of the CT-scan findings from our study do not contrast with those reported in other series (25,26). The CT-scan revealed a 25% sensitivity, and could accurately predict disease outside of the gland in only 28.5% of the cases.

Other studies in the literature have correlated the serum PSA and PSAD with extraprostatic involvement and lymph node metastasis (27, 28, 29, 30). In the 48 patients with localized prostate cancer, the PSAD for patients with positive and negative results on RT-PCR was 0.47 and 0.25 respectively. Recent investigations have demonstrated that a PSAD value greater than 0.3 is associated with a high incidence of extraprostatic disease (31). Our findings of PSA-synthesizing cells in the peripheral circulation of patients circulation of patients with localized prostate cancer and this high PSAD are consistent with this hypothesis.

To our knowledge, this is also the first report employing digoxigenin-labeling as a detection system to enhance the PCR reaction. This enhanced method of detection enabled us to detect an additional 7 patients with localized prostate cancer that would have been missed by conventional ethidium-bromide staining of the agarose gel. We also performed the enhanced detection on all control patient reactions to ensure that these were negative by both techniques, and found that all controls proved negative.

The possibility of staging prostate cancer patients with a 5 cc sample of peripheral blood has several important implications. The future use of such a PCR-based assay has the potential for significantly decreasing the total cost of prostate cancer management. Since this assay appears to be more accurate than current screening modalities, it may enable a reduction not only in the number of preoperative CT-scans and MRI's, but also in the number of radical cancer operations performed. The social and ethical considerations extend to the patient with prostate cancer who may be spared the morbidity of an operation that would otherwise be indicated. And finally, our ability to predict the cure rate in patients undergoing radical cancer surgery will be greatly enhanced with this highly sensitive, accurate test.

REFERENCES

1. Lu-Yao, G., Mclerran, D., Wasson, J., and Wennberg, J. An assessment of radical prostatectomy. *J.A.M.A.* 269:2633–2655 (1993).
2. Epstein, J., Pizov, G., and Walsh, P. C. correlation of pathologic findings after radical retropubic prostatectomy. *Cancer* 71:3582–3593 (1993).
3. Epstein, J., Carmichael, M., Pizov, G., and Walsh, P. C. Influence of capsular penetration on progression following radical prostatectomy: A study of 196 cases with long-term follow-up. *J. Urol.* 150:135–141 (1993).
4. McNeal, J., Villers, A., Redwine, E. A., Freiha, F. S. and Stamey, T. A. Capsular penetration in prostate cancer: Significance for natural history and treatment. *Amer. J. Surg. Path*. 14:240–247 (1990).
5. Anscher, M. S. and Prosnitz. Postoperative radiotherapy for patients with carcinoma of the prostate undergoing radical prostatectomy with positive surgical margins, seminal vesicle involvement and/or penetration through the capsule. *J. Urol.* 138:1407–1412 (1987).
6. Voges, G. E., McNeal, J. E., Redwine, E. A., Freiha, F. S. and Stamey, T. S. Morphologic analysis of surgical margins with positive findings in prostatectomy for adenocarcinoma of the prostate. *Cancer* 69:520–526 (1992).
7. Catalona, W. J., Dresner, S. M. Nerve-sparing radical prostatectomy: Extraprostatic tumor extension and preservation of erectile function. *J. Urol.* 134:1149–1151 (1985).
8. Batson, O. V. The function of the vertebral veins and their role in the spread of metastasis. *Ann. Surg.* 112:138–142 (1940).
9. Dodds, P. R., Caride, V. J., and Lytton, B. The role of the vertebral veins in the dissemination of prostate cancer. *J. Urol.* 126:753–755 (1981).
10. Moreno, J. G., Croce, C. M., Fischer, R., Monne, M., Vihko, P., Mulholland, S. G. and Gomella, L. G. Detection of hematogenous micrometastasis in patients with prostate cancer. *Can. Res.* 52:6110–6112 (1992).
11. Horoszewicz, J. S., Leung, S. S., Kawinski, E., Karr, J. P., Rosenthal, H., Chu, T. M., Mirand, E. A., and Murphy, G. P. LnCaP model of human prostatic carcinoma. *Can. Res.* 43:1809–1817 (1983).
12. Chomezynski, P., and Sacchi, N. Single-step method of RNA isolation by acid guanidinium thiocyanate-phenol-chloroform extraction. *Annal. Biochem.* 162:156–159 (1987).
13. Sanger, F., Nicklen, S., and Coulson, A. R. DNA sequencing with chain-terminating inhibitors. *Proc. Natl. Acad. Sci. USA* 74:5463–5467 (1977).
14. Klobeck, H. G., Combriato, G., Schultz, P., Arbusow, V. and Fittler, F. Genomic sequences of human prostate specific antigen (PSA). *Nucleic Acids Res.* 17:3981–3989 (1989).
15. Sambrook, J., Fritsch, E. F., and Maniatis, T. Molecular Cloning: A Laboratory Manual, Second Edition, (Cold Spring Harbor, N.Y.: Cold Springs Harbor Press) (1989).
16. Benson, M. C., Whang, I. S., Pantuk, A., Ring, K., Kaplan, S. A., Olsson, C. A. and Cooner, W. H. Prostate Specific Antigen Density: A means of distinguishing benign prostatic hypertrophy and prostate cancer. *J. Urol.* 147:815–816 (1992).
17. Wang, M. C., Valenzuela, L. A., Murphy, G. P. and Chu, T. M. Purification of a human prostate specific antigen. *Invest. Urol.* 17:159–164 (1979).
18. Handy, F. C., Lawry, J., Anderson, J. B., Parsons, M. S., Rees, R. C. and Williams, J. L. 1992. Circulating prostate specific antigen-positive cells correlate with metastatic prostate cancer. *Brit. J. Urol.* 69:392–396 (1979).

19. Walsh, P. C. Radical prostatectomy for the treatment of localized prostate cancer. *Urol. Clin. N. Amer.* 7:583–594 (1980).
20. Jewett, H. J., Bridge, H. W., Gray, G. F., and Shelly, W. M. The palpable nodule of prostate cancer. Results of 15 years after radical excision. *J.A.M.A.* 203:403–144 (1968).
21. Mukamel, E., Hanna, J., and deKernion, J. B. Staging errors in clinically localized prostate cancer. *Urol.* 30:318–323 (1982).
22. Rosen, M. A., Goldstone, L. Lapin, S., Wheeler, T., and Scardino, P. Frequency and location of extracapsular extension and positive surgical margins in radical prostatectomy specimens. *J. Urol.* 148:331–337 (1192).
23. Rifkin, M. D., Zerhouni, E. A., Gatsonis, C. A., Quint, L. E., Paushter, D. M. et al. Comparison of magnetic resonance imaging and ultrasonography in staging early prostate cancer. *New Eng. J. Med.* 323:621–626 (1990).
24. Platt, J. F., Bree, R. L. and Schwab, R. E. The accuracy of CT in the staging of the prostate. *Amer. J. Roent.* 149:315–318 (1987).
25. Salo, J. O., Kivisaari, L., Rannikko, S. and Lehtonen, T. Computerized tomography and transrectal ultrasound in the assessment of local extension of prostatic carcinoma before radical retropubic prostatectomy. *J. Urol.* 137:435–438 (1987).
26. Hricak, H., et al. Prostatic carcinoma: Staging by clinical assessment, CT, and MR imaging. *Radiology* 162:331–335 (1987).
27. Oesterling, J., Martin, S., Bergstralh, E. and Lowe, F. C. The use of prostate specific antigen in staging patients with newly diagnosed prostate cancer. *J.A.M.A* 269:57–60 (1993).
28. Winter, H. I., Bretton, P. R. and Herr, H. W. Preoperative prostate-specific antigen in predicting pathological stage and grade after radical prostatectomy. *Urology* 38:202–205 (1991).
29. Hudson, M. A., Bahnson, R. R., and Catalona, W. J. Clinical use of prostate specific antigen density in patients with prostate cancer. *J. Urol.* 142:1011–1017 (1989).
30. Gerber, G. S., and Goldberg, R., and Chodak, G. W. Local staging of prostate cancer by tumor volume, prostate-specific antigen, and transrectal ultrasound. *Urology* 40:311–316 (1992).
31. Seaman, E., Kistler, S., Katz, A. E. and Benson, M. C. The use of PSAD to predict D-0 prostatic carcinoma. *J. Urol.* 149:300A (1993).

What is claimed is:

1. A method of determining the presence of mRNA encoding the PSA protein in a sample from a human subject which comprises:
(a) collecting a sample of peripheral blood from the subject;
(b) extracting mRNA molecules from the peripheral blood;
(c) amplifying a cDNA molecule encoding the PSA protein which comprises:
(I) contacting the mRNA molecule extract with a nucleic acid molecule primer capable of specifically hybridizing to a nucleic acid sequence site included within the mRNA encoding the PSA protein under conditions allowing the primer to specifically hybridize to the mRNA encoding the PSA protein;
(ii) contacting the composition produced by (I) with reverse transcriptase under conditions allowing the reverse transcriptase to transcribe a single stranded cDNA molecule copy of the mRNA molecule encoding the PSA protein;
(iii) heat denaturing the cDNA and mRNA molecule of composition produced by step (ii);
(iv) contacting the composition produced by step (iii) with a first primer capable of specifically hybridizing to a first unique nucleic acid molecule sequence site located on the cDNA molecule complementary to the mRNA encoding the PSA protein under conditions allowing the first primer to specifically hybridize with the first unique nucleic acid molecule sequence site;
(v) contacting the composition produced by step (iv) with DNA polymerase under conditions allowing the DNA polymerase to synthesize a double stranded cDNA molecule encoding the PSA protein using the first primer to initiate synthesis and the single-stranded cDNA molecule as a template;
(vi) heat denaturing the double-stranded cDNA molecule of the composition produced by step (v);
(vii) contacting the composition produced by step (vi) with the first primer and a second nucleic acid molecule primer capable of specifically hybridizing with a second unique nucleic acid sequence site is located on the other cDNA strand 3' of the first unique site under conditions allowing the first and second primers to specifically hybridize with the first and second unique sequences, respectively, of the cDNA molecule, encoding the PSA protein;
(viii) contacting the composition produced by step (vii) with DNA polymerase under conditions allowing the DNA polymerase to synthesis cDNA molecules encoding the PSA protein using the first or second primers to initiate synthesis and the heat denatured cDNA molecule encoding the PSA protein as a template; and
(ix) repeating steps (vi) through (viii) for at least twenty five times; and
(d) detecting the presence of the cDNA molecule encoding the PSA protein and by:

(a') adding digoxigenin-labeled nucleotides in step (iv);
(b') loading the composition of step (ix) which contains digoxigenin-labeled nucleotides onto a gel;
(c') electrophoresing the cDNA into the gel with a digoxigenin-labeled DNA ladder;
(d') transferring and fixing the DNA in the gel onto a membrane;
(e') contacting the DNA on the membrane with an antibody which specifically binds digoxigenin, wherein the antibody is linked to an enzyme capable of directly or indirectly activating a chemiluminescent substrate;
(f') contacting the antibody bound DNA with the activatable chemiluminescent substrate;
(g') visualizing the presence of labeled DNA by exposing the membrane to a light sensitive device; and
(h') detecting the presence of the cDNA molecule encoding the PSA protein and thereby determining the stage of prostate cancer.

2. The method of claim 1, wherein the enzyme capable of activating a chemiluminescent substrate is alkaline phosphatase, the chemiluminescent substrate is 4-methoxy-4-(3-phosphate-phenyl)-spriro(1,2-dioxetane-3,2-adamantane) disodium salt, and the light sensitive device is X-ray film.

3. A method of determining the presence of mRNA encoding the PSA protein in a sample from a human subject which comprises:
(a) collecting a sample of peripheral blood from the subject;
(b) extracting mRNA molecules from the peripheral blood;
(c) amplifying a cDNA molecule encoding the PSA protein which comprises:
(i) contacting the mRNA molecule extract with a nucleic acid molecule primer capable of specifically hybridizing to a nucleic acid sequence site included within the mRNA encoding the PSA protein under conditions allowing the primer to specifically hybridize to the mRNA encoding the PSA protein;
(ii) contacting the composition produced by (i) with reverse transcriptase under conditions allowing the reverse transcriptase to transcribe a single stranded cDNA molecule copy of the mRNA molecule encoding the PSA protein;
(iii) heat denaturing the cDNA and mRNA molecule of composition produced by step (ii);
(iv) contacting the composition produced by step (iii) with a first primer comprised of a nucleic acid molecule with a nucleotide sequence of 5' GATGACTCCAGCCACGACCT 3' (SEQ. ID. NO:4) under conditions allowing the first primer to specifically hybridize with the first unique nucleic acid molecule sequence site;
(v) contacting the composition produced by step (iv) with DNA polymerase under conditions allowing the DNA polymerase to synthesize a double stranded cDNA molecule encoding the PSA protein using the first primer to initiate synthesis and the single-stranded cDNA molecule as a template;

(vi) heat denaturing the double-stranded cDNA molecule of the composition produced by step (v);

(vii) contacting the composition produced by step (vi) with the first primer and a second nucleic acid molecule primer capable of specifically hybridizing with a second unique nucleic acid sequence site is located on the other cDNA strand 3' of the first unique site under conditions allowing the first and second primers to specifically hybridize with the first and second unique sequences, respectively, of the cDNA molecule, encoding the PSA protein;

(viii) contacting the composition produced by step (vii) with DNA polymerase under conditions allowing the DNA polymerase to synthesis cDNA molecules encoding the PSA protein using the first or second primers to initiate synthesis and the heat denatured cDNA molecule encoding the PSA protein as a template; and (ix) repeating steps (vi) through (viii) for at least twenty five times; and (d) detecting the presence of the cDNA molecule encoding the PSA protein and thereby determining the presence of mRNA encoding the PSA protein.

4. A method of determining the presence of mRNA encoding the PSA protein in a sample from a human subject which comprises:

(a) collecting a sample of peripheral blood from the subject;

(b) extracting mRNA molecules from the peripheral blood;

(c) amplifying a cDNA molecule encoding the PSA protein which comprises:

(i) contacting the mRNA molecule extract with a nucleic acid molecule primer capable of specifically hybridizing to a nucleic acid sequence site included within the mRNA encoding the PSA protein under conditions allowing the primer to specifically hybridize to the mRNA encoding the PSA protein;

(ii) contacting the composition produced by (i) with reverse transcriptase under conditions allowing the reverse transcriptase to transcribe a single stranded cDNA molecule copy of the mRNA molecule encoding the PSA protein;

(iii) heat denaturing the cDNA and mRNA molecule of composition produced by step (ii);

(iv) contacting the composition produced by step (iii) with a first primer capable of specifically hybridizing to a first unique nucleic acid molecule sequence site located on the cDNA molecule complementary to the mRNA encoding the PSA protein under conditions allowing the first primer to specifically hybridize with the first unique nucleic acid molecule sequence site;

(v) contacting the composition produced by step (iv) with DNA polymerase under conditions allowing the DNA polymerase to synthesize a double stranded cDNA molecule encoding the PSA protein using the first primer to initiate synthesis and the single-stranded cDNA molecule as a template;

(vi) heat denaturing the double-stranded cDNA molecule of composition produced by step (v);

(vii) contacting the composition produced by step (vi) with the first primer and a second nucleic acid molecule primer comprised of a nucleic acid molecule with a nucleotide sequence of 5' CACAGACACCCCATCCTATC 3' (SEQ. ID. NO:3) capable of specifically hybridizing with a second unique nucleic acid sequence site is located on the other cDNA strand 3' of the first unique site under conditions allowing the first and second primers to specifically hybridize with the first and second unique sequences, respectively, of the cDNA molecule, encoding the PSA protein;

(viii) contacting the composition produced by step (vii) with DNA polymerase under conditions allowing the DNA polymerase to synthesis cDNA molecules encoding the PSA protein using the first or second primers to initiate synthesis and the heat denatured cDNA molecule encoding the PSA protein as a template; and (ix) repeating steps (vi) through (viii) for at least twenty five times; and (d) detecting the presence of the cDNA molecule encoding the PSA protein and thereby determining the presence of mRNA encoding the PSA protein.

5. The method of claim 3, wherein the second primer comprises a nucleic acid molecule with a nucleotide sequence of 5' CACAGACACCCCATCCTATC 3' (SEQ. ID. NO:3) and the amplified cDNA detected is 710 base pairs long.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 1729 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( i x ) FEATURE:
        ( A ) NAME/KEY: CDS
        ( B ) LOCATION: 378..1088

( x i ) SEQUENCE DESCRIPTION: SEQ ID NO:1:

```
AAGTTTCCCT  TCTCCCAGTC  CAAGACCCCA  AATCACCACA  AAGGACCCAA  TCCCCAGACT           60

CAAGATATGG  TCTGGGCGCT  GTCTTGTGTC  TCCTACCCTG  ATCCCTGGGT  TCAACTCTGC          120

TCCCAGAGCA  TGAAGCCTCT  CCACCAGCAC  CAGCCACCAA  CCTGCAAACC  TAGGGAAGAT          180

TGACAGAATT  CCCAGCCTTT  CCCAGCTCCC  CCTGCCCATG  TCCCAGGACT  CCCAGCCTTG          240

GTTCTCTGCC  CCCGTGTCTT  TTCAAACCCA  CATCCTAAAT  CCATCTCCTA  TCCGAGTCCC          300

CCAGTTCCTC  CTGTCAACCC  TGATTCCCCT  GATCTAGCAC  CCCCTCTGCA  GGTGCTGCAC          360

CCCTCATCCT  GTCTCGG ATT  GTG  GGA  GGC  TGG  GAG  TGC  GAG  AAG  CAT  TCC       410
                    I l e  V a l  G l y  G l y  T r p  G l u  C y s  G l u  L y s  H i s  S e r
                       1                    5                               1 0

CAA  CCC  TGG  CAG  GTG  CTT  GTA  GCC  TCT  CGT  GGC  AGG  GCA  GTC  TGC  GGC  458
G l n  P r o  T r p  G l n  V a l  L e u  V a l  A l a  S e r  A r g  G l y  A r g  A l a  V a l  C y s  G l y
                1 5                         2 0                          2 5

GGT  GTT  CTG  GTG  CAC  CCC  CAG  TGG  GTC  CTC  ACA  GCT  ACC  CAC  TGC  ATC  506
G l y  V a l  L e u  V a l  H i s  P r o  G l n  T r p  V a l  L e u  T h r  A l a  T h r  H i s  C y s  I l e
```

```
             30                         35                         40
AGG  AAC  AAA  AGC  GTG  ATC  TTG  CTG  GGT  CGG  CAC  AGC  CTG  TTT  CAT  CCT      554
Arg  Asn  Lys  Ser  Val  Ile  Leu  Leu  Gly  Arg  His  Ser  Leu  Phe  His  Pro
          45                       50                     55

GAA  GAC  ACA  GGC  CAG  GTA  TTT  CAG  GTC  AGC  CAC  AGC  TTC  CCA  CAC  CCG      602
Glu  Asp  Thr  Gly  Gln  Val  Phe  Gln  Val  Ser  His  Ser  Phe  Pro  His  Pro
 60                      65                     70                          75

CTC  TAC  GAT  ATG  AGC  CTC  CTG  AAG  AAT  CGA  TTC  CTC  AGG  CCA  GGT  GAT      650
Leu  Tyr  Asp  Met  Ser  Leu  Leu  Lys  Asn  Arg  Phe  Leu  Arg  Pro  Gly  Asp
               80                          85                         90

GAC  TCC  AGC  CAC  GAC  CTC  ATG  CTG  CTC  CGC  CTG  TCA  GAG  CCT  GCC  GAG      698
Asp  Ser  Ser  His  Asp  Leu  Met  Leu  Leu  Arg  Leu  Ser  Glu  Pro  Ala  Glu
               95                         100                    105

CTC  ACG  GAT  GCT  ATG  AAG  GTC  ATG  GAC  CTG  CCC  ACC  CAG  GAG  CCA  GCA      746
Leu  Thr  Asp  Ala  Met  Lys  Val  Met  Asp  Leu  Pro  Thr  Gln  Glu  Pro  Ala
         110                         115                    120

CTG  GGG  ACC  ACC  TGC  TAC  GCC  TCA  GGC  TGG  GGC  AGC  ATT  GAA  CCA  GAG      794
Leu  Gly  Thr  Thr  Cys  Tyr  Ala  Ser  Gly  Trp  Gly  Ser  Ile  Glu  Pro  Glu
    125                        130                         135

GAG  TTC  TTG  ACC  CCA  AAG  AAA  CTT  CAG  TGT  GTG  GAC  CTC  CAT  GTT  ATT      842
Glu  Phe  Leu  Thr  Pro  Lys  Lys  Leu  Gln  Cys  Val  Asp  Leu  His  Val  Ile
140                          145                    150                    155

TCC  AAT  GAC  GTG  TGT  GCG  CAA  GTT  CAC  CCT  CAG  AAG  GTG  ACC  AAG  TTC      890
Ser  Asn  Asp  Val  Cys  Ala  Gln  Val  His  Pro  Gln  Lys  Val  Thr  Lys  Phe
                    160                    165                         170

ATG  CTG  TGT  GCT  GGA  CGC  TGG  ACA  GGG  GGC  AAA  AGC  ACC  TGC  TCG  GGT      938
Met  Leu  Cys  Ala  Gly  Arg  Trp  Thr  Gly  Gly  Lys  Ser  Thr  Cys  Ser  Gly
              175                         180                    185

GAT  TCT  GGG  GGC  CCA  CTT  GTC  TGT  AAT  GGT  GTG  CTT  CAA  GGT  ATC  ACG      986
Asp  Ser  Gly  Gly  Pro  Leu  Val  Cys  Asn  Gly  Val  Leu  Gln  Gly  Ile  Thr
         190                         195                    200

TCA  TGG  GGC  AGT  GAA  CCA  TGT  GCC  CTG  CCC  GAA  AGG  CCT  TCC  CTG  TAC     1034
Ser  Trp  Gly  Ser  Glu  Pro  Cys  Ala  Leu  Pro  Glu  Arg  Pro  Ser  Leu  Tyr
    205                        210                         215

ACC  AAG  GTG  GTG  CAT  TAC  CGG  AAG  TGG  ATC  AAG  GAC  ACC  ATC  GTG  GCC     1082
Thr  Lys  Val  Val  His  Tyr  Arg  Lys  Trp  Ile  Lys  Asp  Thr  Ile  Val  Ala
220                          225                    230                    235

AAC  CCC  TGAGCACCCC  TATCAACTCC  CTATTGTAGT  AAACTTGGAA  CCTTGGAAAT           1138
Asn  Pro

GACCAGGCCA  AGACTCAGGC  CTCCCCAGTT  CTACTGACCT  TTGTCCTTAG  GTGTGAGGTC           1198

CAGGGTTGCT  AGGAAAAGAA  ATCAGCAGAC  ACAGGTGTAG  ACCAGAGTGT  TTCTTAAATG           1258

GTGTAATTTT  GTCCTCTCTG  TGTCCTGGGG  AATACTGGCC  ATGCCTGGAG  ACATATCACT           1318

CAATTTCTCT  GAGGACACAG  ATAGGATGGG  GTGTCTGTGT  TATTTGTGGG  GTACAGAGAT           1378

GAAAGAGGGG  TGGGATCCAC  ACTGAGAGAG  TGGAGAGTGA  CATGTGCTGG  ACACTGTCCA           1438

TGAAGCACTG  AGCAGAAGCT  GGAGGCACAA  CGCACCAGAC  ACTCACAGCA  AGGATGGAGC           1498

TGAAAACATA  ACCCACTCTG  TCCTGGAGGC  ACTGGGAAGC  CTAGAGAAGG  CTGTGAACCA           1558

AGGAGGGAGG  GTCTTCCTTT  GGCATGGGAT  GGGGATGAAG  TAAGGAGAGG  GACTGACCCC           1618

CTGGAAGCTG  ATTCACTATG  GGGGAGGTG  TATTGAAGTC  CTCCAGACAA  CCCTCAGATT           1678

TGATGATTTC  CTAGTAGAAC  TCACAGAAAT  AAAGAGCTGT  TATACTGTGA  A                    1729
```

( 2 ) INFORMATION FOR SEQ ID NO:2:

( i ) SEQUENCE CHARACTERISTICS:
        ( A ) LENGTH: 237 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| Ile | Val | Gly | Gly | Trp | Glu | Cys | Glu | Lys | His | Ser | Gln | Pro | Trp | Gln | Val |
|---|---|---|---|---|---|---|---|---|---|---|---|---|---|---|---|
| 1 | | | | 5 | | | | | 10 | | | | | 15 | |

| Leu | Val | Ala | Ser | Arg | Gly | Arg | Ala | Val | Cys | Gly | Gly | Val | Leu | Val | His |
|---|---|---|---|---|---|---|---|---|---|---|---|---|---|---|---|
| | | | 20 | | | | | 25 | | | | | 30 | | |

| Pro | Gln | Trp | Val | Leu | Thr | Ala | Thr | His | Cys | Ile | Arg | Asn | Lys | Ser | Val |
|---|---|---|---|---|---|---|---|---|---|---|---|---|---|---|---|
| | | 35 | | | | | 40 | | | | | 45 | | | |

| Ile | Leu | Leu | Gly | Arg | His | Ser | Leu | Phe | His | Pro | Glu | Asp | Thr | Gly | Gln |
|---|---|---|---|---|---|---|---|---|---|---|---|---|---|---|---|
| | 50 | | | | | 55 | | | | | 60 | | | | |

| Val | Phe | Gln | Val | Ser | His | Ser | Phe | Pro | His | Pro | Leu | Tyr | Asp | Met | Ser |
|---|---|---|---|---|---|---|---|---|---|---|---|---|---|---|---|
| 65 | | | | | 70 | | | | | 75 | | | | | 80 |

| Leu | Leu | Lys | Asn | Arg | Phe | Leu | Arg | Pro | Gly | Asp | Asp | Ser | Ser | His | Asp |
|---|---|---|---|---|---|---|---|---|---|---|---|---|---|---|---|
| | | | | 85 | | | | | 90 | | | | | 95 | |

| Leu | Met | Leu | Leu | Arg | Leu | Ser | Glu | Pro | Ala | Glu | Leu | Thr | Asp | Ala | Met |
|---|---|---|---|---|---|---|---|---|---|---|---|---|---|---|---|
| | | | 100 | | | | | 105 | | | | | 110 | | |

| Lys | Val | Met | Asp | Leu | Pro | Thr | Gln | Glu | Pro | Ala | Leu | Gly | Thr | Thr | Cys |
|---|---|---|---|---|---|---|---|---|---|---|---|---|---|---|---|
| | | 115 | | | | | 120 | | | | | 125 | | | |

| Tyr | Ala | Ser | Gly | Trp | Gly | Ser | Ile | Glu | Pro | Glu | Glu | Phe | Leu | Thr | Pro |
|---|---|---|---|---|---|---|---|---|---|---|---|---|---|---|---|
| | 130 | | | | | 135 | | | | | 140 | | | | |

| Lys | Lys | Leu | Gln | Cys | Val | Asp | Leu | His | Val | Ile | Ser | Asn | Asp | Val | Cys |
|---|---|---|---|---|---|---|---|---|---|---|---|---|---|---|---|
| 145 | | | | | 150 | | | | | 155 | | | | | 160 |

| Ala | Gln | Val | His | Pro | Gln | Lys | Val | Thr | Lys | Phe | Met | Leu | Cys | Ala | Gly |
|---|---|---|---|---|---|---|---|---|---|---|---|---|---|---|---|
| | | | | 165 | | | | | 170 | | | | | 175 | |

| Arg | Trp | Thr | Gly | Gly | Lys | Ser | Thr | Cys | Ser | Gly | Asp | Ser | Gly | Gly | Pro |
|---|---|---|---|---|---|---|---|---|---|---|---|---|---|---|---|
| | | | 180 | | | | | 185 | | | | | 190 | | |

| Leu | Val | Cys | Asn | Gly | Val | Leu | Gln | Gly | Ile | Thr | Ser | Trp | Gly | Ser | Glu |
|---|---|---|---|---|---|---|---|---|---|---|---|---|---|---|---|
| | | 195 | | | | | 200 | | | | | 205 | | | |

| Pro | Cys | Ala | Leu | Pro | Glu | Arg | Pro | Ser | Leu | Tyr | Thr | Lys | Val | Val | His |
|---|---|---|---|---|---|---|---|---|---|---|---|---|---|---|---|
| | 210 | | | | | 215 | | | | | 220 | | | | |

| Tyr | Arg | Lys | Trp | Ile | Lys | Asp | Thr | Ile | Val | Ala | Asn | Pro |
|---|---|---|---|---|---|---|---|---|---|---|---|---|
| 225 | | | | | 230 | | | | | 235 | | |

( 2 ) INFORMATION FOR SEQ ID NO:3:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:3:

CACAGACACC CCATCCTATC        20

( 2 ) INFORMATION FOR SEQ ID NO:4:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:

(A) ORGANISM: Homo sapiens (xi) SEQUENCE DESCRIPTION: SEQ ID NO:4:

GATGACTCCA GCCACGACCT 20